(12) United States Patent
Yen et al.

(10) Patent No.: US 8,138,165 B2
(45) Date of Patent: Mar. 20, 2012

(54) CHROMONES AND CHROMONE DERIVATIVES AND USES THEREOF

(75) Inventors: Mao-Hsiung Yen, Taipei (TW); Edwin S. C. Wu, Cary, NC (US)

(73) Assignee: Jenken Biosciences, Inc., Cary, NC (US)

( * ) Notice: Subject to any disclaimer, the term of this patent is extended or adjusted under 35 U.S.C. 154(b) by 0 days.

(21) Appl. No.: 10/531,506

(22) PCT Filed: Oct. 22, 2003

(86) PCT No.: PCT/US03/33578
§ 371 (c)(1),
(2), (4) Date: Oct. 3, 2005

(87) PCT Pub. No.: WO2004/037193
PCT Pub. Date: May 6, 2004

(65) Prior Publication Data
US 2006/0142211 A1    Jun. 29, 2006

Related U.S. Application Data

(60) Provisional application No. 60/420,306, filed on Oct. 22, 2002, provisional application No. 60/453,771, filed on Mar. 11, 2003.

(51) Int. Cl.
*A61K 31/665* (2006.01)
*C07D 311/00* (2006.01)
(52) U.S. Cl. ........................................ 514/100; 549/403
(58) Field of Classification Search .................. 549/403
See application file for complete search history.

(56) References Cited

U.S. PATENT DOCUMENTS 5,756,538 A * 5/1998 Cassels et al. ................ 514/456
6,224,872 B1   5/2001 Shibnya et al.
6,541,613 B2 * 4/2003 Hendler et al. ................... 536/8

FOREIGN PATENT DOCUMENTS
WO    WO 01/30342 A1 * 5/2001
* cited by examiner

*Primary Examiner* — Elli Peselev
(74) *Attorney, Agent, or Firm* — Ladas & Parry LLP

(57) ABSTRACT

Certain 2- and/or 3-substituted 5,6,7 substituted chromones are of use in treatment of treating diseases associated with overproduction of TNF-α, diseases associated with overproduction of superoxide anion radical And the treatment of organ damage. Some of the compounds are novel.

10 Claims, 9 Drawing Sheets

Fig. 1 Time-dependent effects of Compound 11a on mean arterial pressure in LPS-treated rats (n=7) (iv)
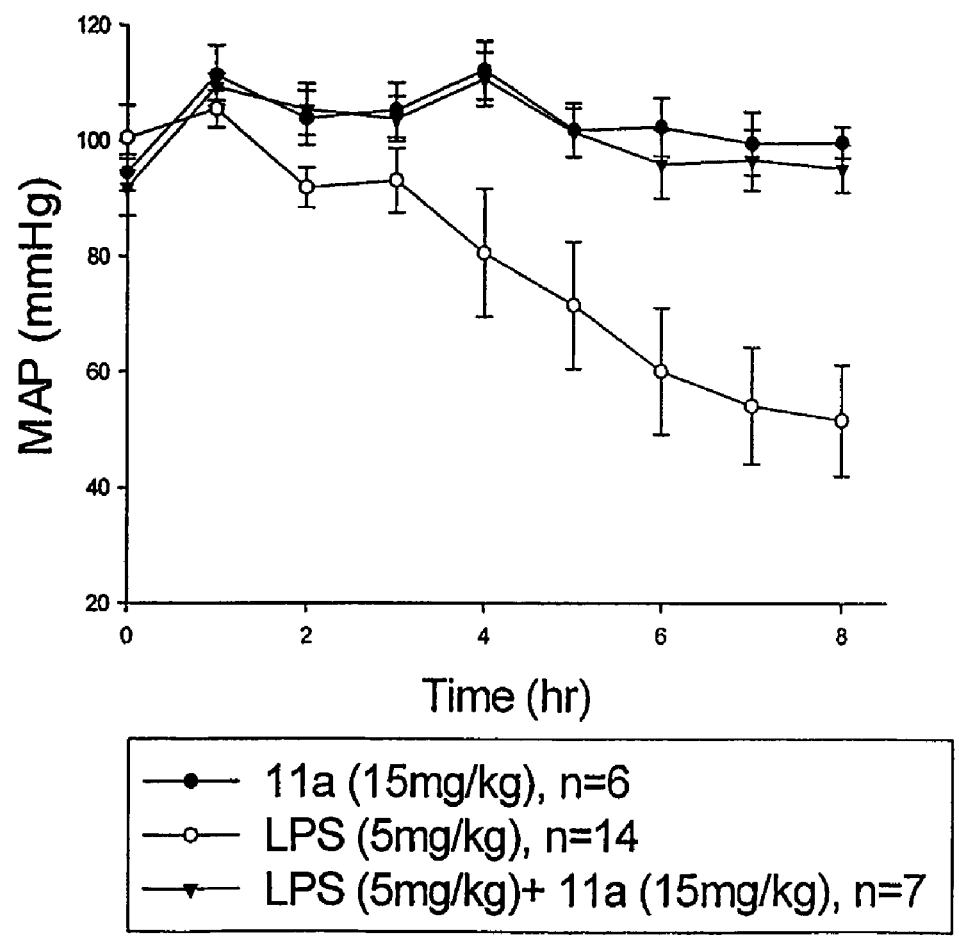

Fig. 2 Time-dependent effects of Compound 11a on heart rates in LPS-treated rats (n=8) (iv)
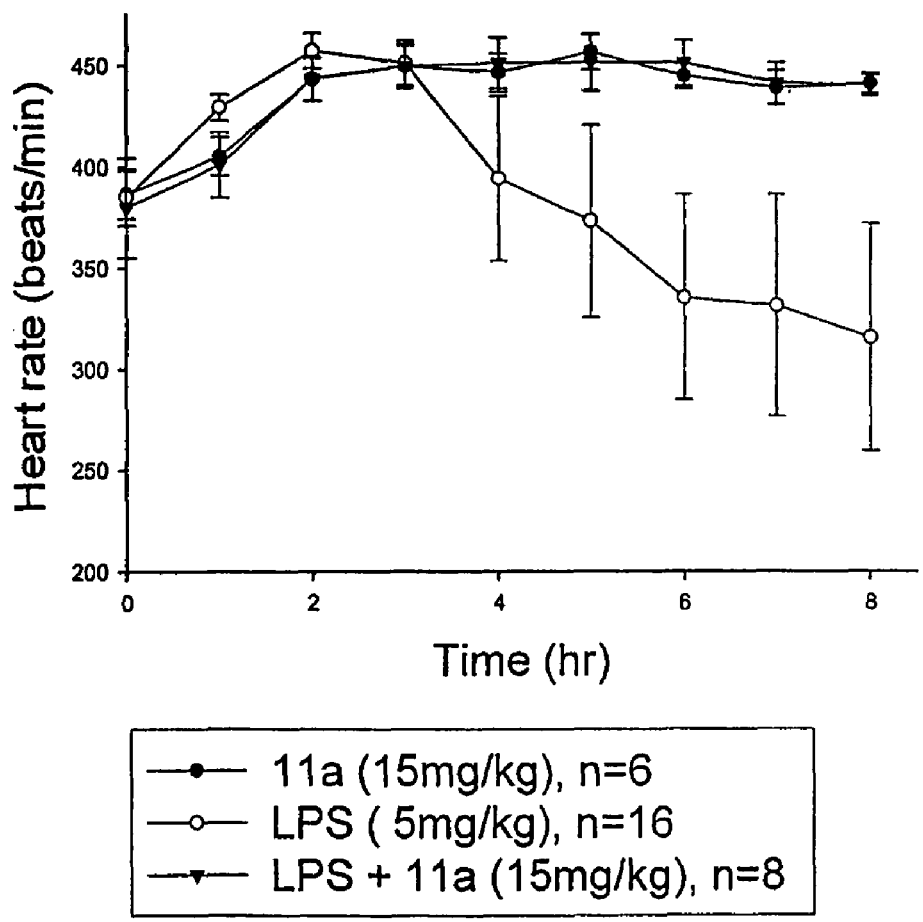

Fig. 3 Effects of Compound 11a on the plasma TNF-α level in LPS-treated rats
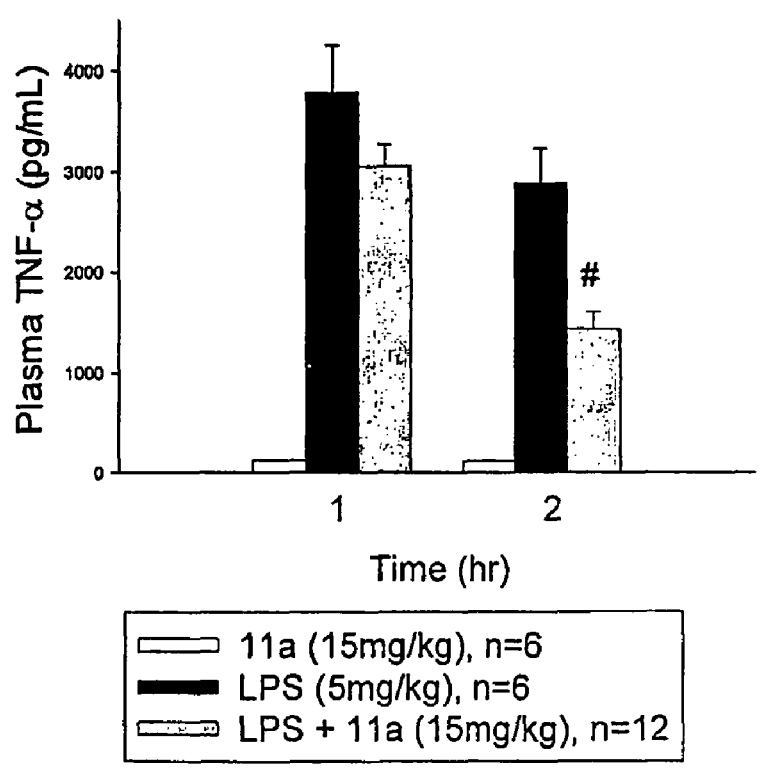

Fig. 4 Effects of Compound 11a on superoxide anion production in aortic tissue of LPS-treated rats 8 hr after dosing
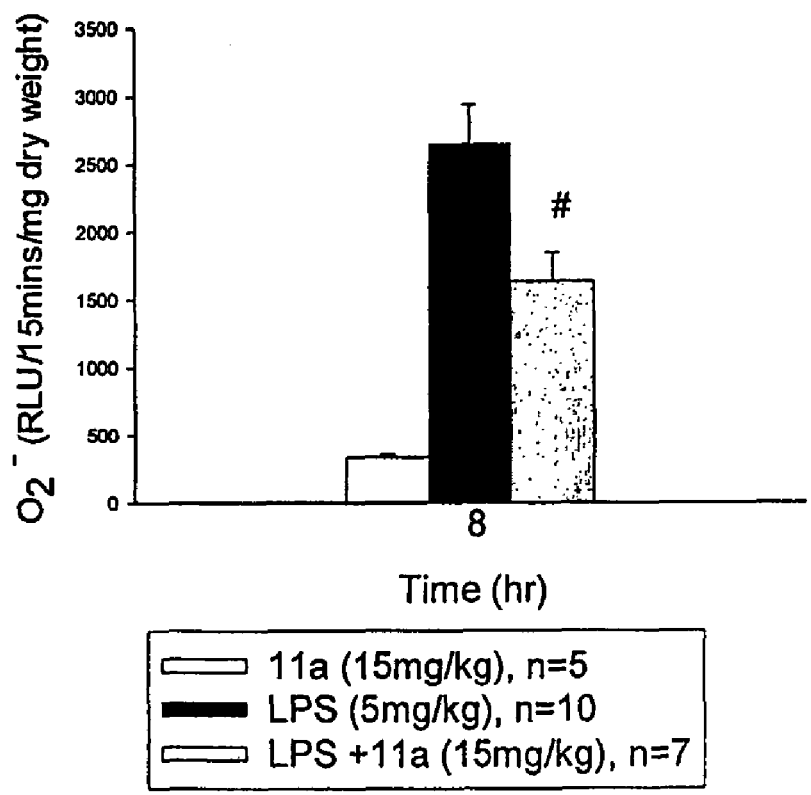

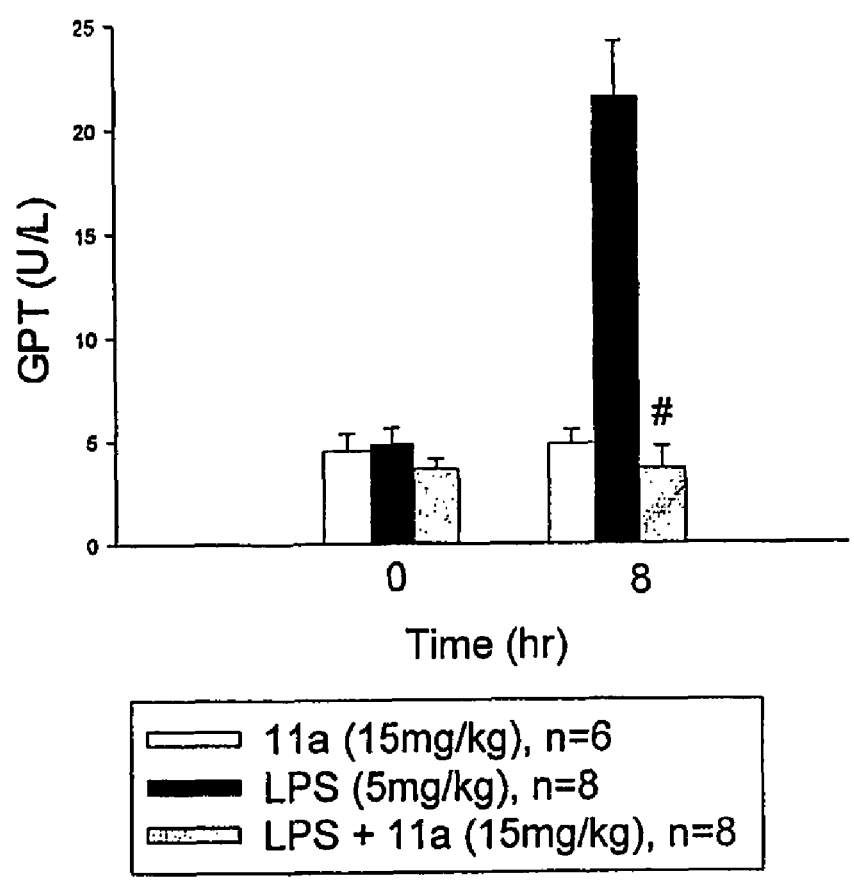
Fig. 5 Effects of Compound 11a on SGPT level in LPS-treated rats 8 hr after dosing

Fig. 6 Effects of Compound 11a on SGOT level in LPS-treated rats 8 hr after dosing
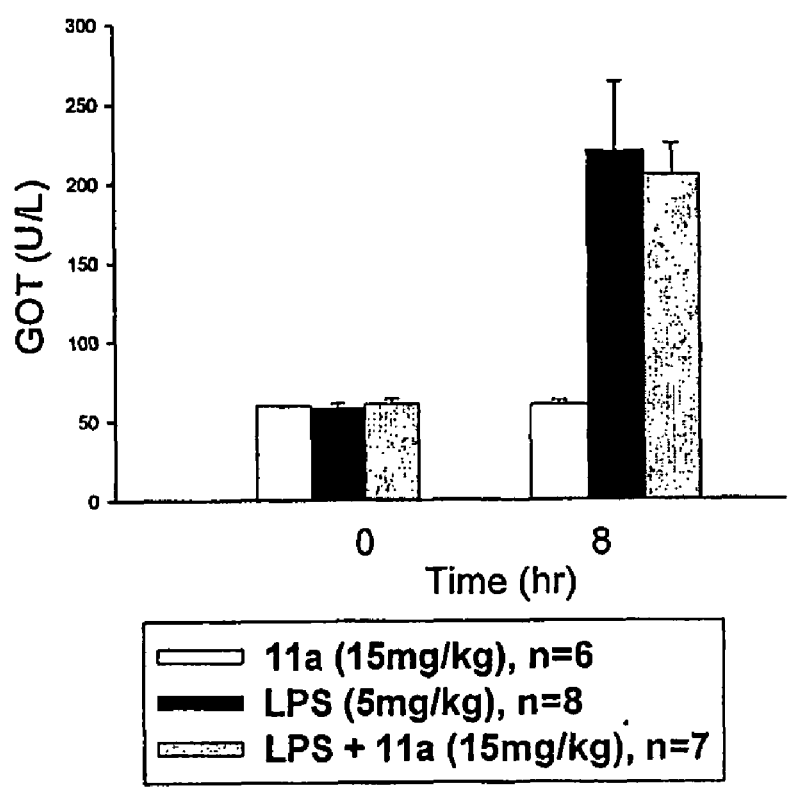

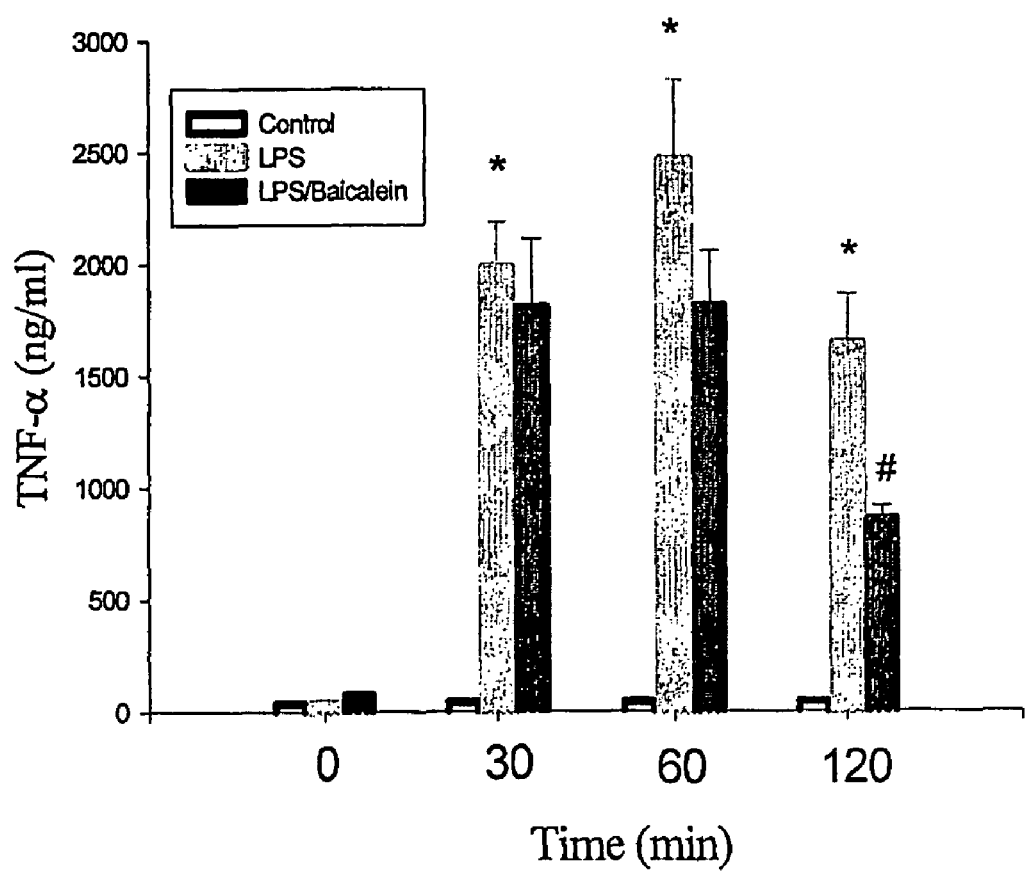
Fig. 7 Effects of baicalein on the plasma TNF-α level in LPS-treated rats (20 mg/kg, iv)

Fig. 8 Effects of baicalein on superoxide anion production in aortic tissue of LPS-treated rats 6 hr after dosing
(20 mg/kg, iv)
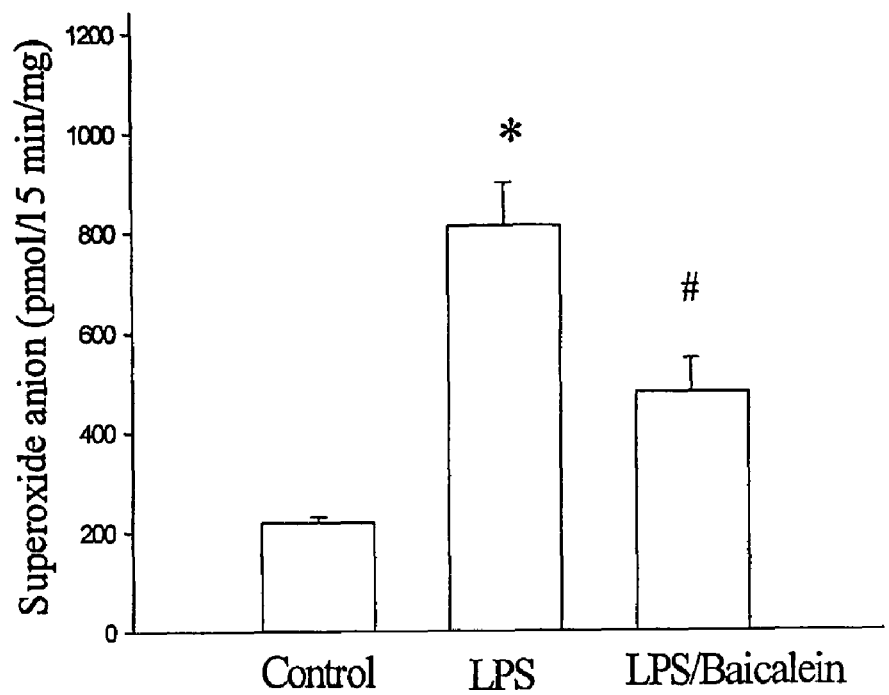

Fig. 9 Effects of Compound 11a on lung tissues LPS-treated rats 8 hr after dosing

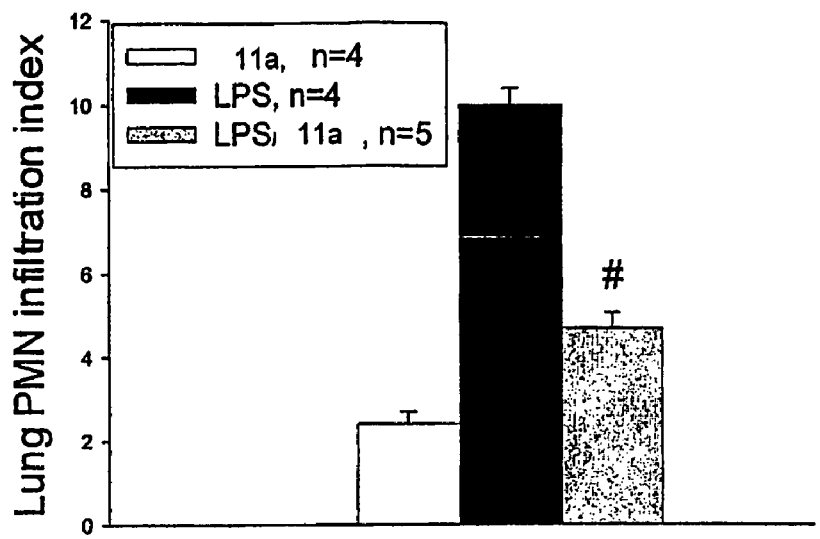

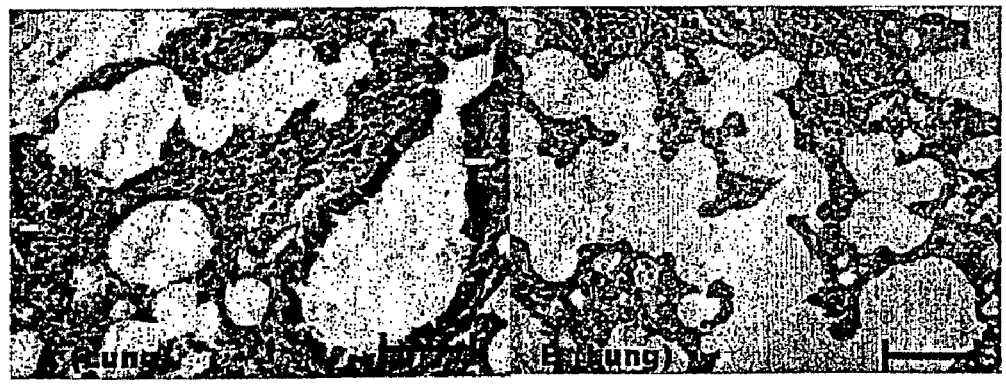

Histopathological studies at the high power (400x) of the light microscope showed morphologically relative normal lung tissues form the groups of the rats, marked PMN infiltration (arrow) in the groups of the rats which received infiltration of lipopolysaccharide (LPS,A), that was improved in the compound 11a posttreatment groups (B).Bars=50µm.

CHROMONES AND CHROMONE DERIVATIVES AND USES THEREOF

RELATED APPLICATION DATA

This application claims the benefit of U.S. Provisional Application Ser. No. 60/420,306, filed Oct. 22, 2002, and U.S. Provisional Application Ser. No. 60/453,771, filed Mar. 11, 2003, the disclosures of which are incorporated herein by reference in their entireties.

FIELD OF THE INVENTION

The present invention concerns chromones, novel chromone derivatives, and pharmaceutical formulations thereof, and use thereof for prevention and treatment of disorders such as septic shock and organ damage.

BACKGROUND OF THE INVENTION

Septic shock can be defined as a spectrum of clinical conditions caused by the immune response of a host to infection or trauma characterized by systemic inflammation and coagulation (Mesters R M, et al. Increase of plasminogen activator inhibitor levels predicts outcome of leukocytopenic patients and sepsis. *Thromb Haemost.* 1996a; 75: 902-907; Wheeler A P and Bernard G R. Treating patients with severe sepsis. *N Engl J Med* 340: 207-214 (1999)). Conditions range from a systemic inflammatory response to organ dysfunction to multiple organ failure, and ultimately death. In elderly, immunocompromised, and critically ill patients, septic shock is a major cause of morbidity and mortality in intensive care units worldwide (Friedman G, et al. Has the mortality of septic shock changed with time? *Crit Care Med.* 26:2078-2086 (1998)). In the United States, septic shock is the leading cause of death in noncoronary intensive care unit (ICU) patients (Sands K E, et al. Epidemiology of sepsis syndrome in 8 academic medical centers. *JAMA* 278: 234-240 (1997)). Additionally, 1998 data from the Centers for Disease Control show that septic shock is the 11th leading cause of death overall (National Vital Statistics Report, 2000).

Flavonoids or bioflavonoids encompass a ubiquitous group of polyphenolic substances that are present in most plants, concentrated in seeds, fruit skin or peel, bark, and flowers. Various classes of flavonoids include the following: flavanols, flavanones, flavones (2-phenylchrmones), flavan-3-ols (catechins), anthocyanins, and isoflavones (3-phenylchrmones). Baicalein, baicalin, and wogonin (shown below) are known bioactive flavonoids of *Scutellaria baicalensis* GEORGI. In recent studies, baicalein, baicalin, and wogonin have been reported to show anti-inflammatory [Bao, Q L et al. The flavonoid baicalin exhibits anti-inflammatory activity by binding to chemokines. *Immunopharmacology.* 49: 295-306 (2000); Wakabayashi I and Yasui K Wogonin inhibits inducible prostaglandin $E_2$ production in macrophages. *Eur J Pharmacol.* 406: 477481 (2000); Kimura et al. Effects of baicalein isolated from *Scutellaria baicalensis* on interleukin 1 β- and tumor necrosis factor α-induced adhesion molecule expression in cultured human umbilical vein endothelial cells. *J Ethnopharmacol.* 57: 63-67 (1997); and Lin C C and Shieh D E The anti-inflammatory activity of *Scutellaria rivularis* extracts and its active components, baicalin, baicalein and wogonin. *Am J Chin Med.* 24: 31-36 (1996)], anti-allergic (Kyo et al. Baicalin and baicalein, constituents of an important medicinal plant, inhibit intracellular $Ca^{2+}$ elevation by reducing phospholipase C activity in C6 rat glioma cells. *J Pharm Pharmacol.* 50: 1179-1182 (1998); Gao et al. Free radical scavenging and antioxidant activities of flavonoids extracted from the radix of *Scutellaria baicalensis* Georgi. *Biochemica et Biophysica Acta B.* 1472: 643-650 (1999); Gabrielska J Antioxidant activity of flavones from *Scutellaria baicalensis* in lecithin liposomes. *J Biosci.* 52: 817-823 (1997)], antioxidant [Shieh et al. Antioxidant and free radical scavenging effects of baicalein, baicalin, and wogonin. *Anticancer Res.* 20: 2861-2865 (2000)], and anticancer activities [Ikemoto S et al. Antitumor effects of *Scutellariae Radix* and its components baicalein, baicalin, and wogonin on bladder cancer cell lines. *Urology* 55: 951-955 (2000); Chan F L et al. Induction of apoptosis in prostate cancer cell lines by flavonoid, baicalin. *Cancer Lett.* (2000)]. Moreover, baicalin has been shown to possess antiviral activity [Nagai T et al. Mode of action of the anti-influenza virus activity of plant flavonoid, 5,7,4'-trihydroxy-8-methoxyflavone, from the roots of *Scutellaria baicalensis. Antiviral Res.* 26: 11-25 (1995); Nagai T et al. Mode of action of the anti-influenza virus activity of plant flavonoid, 5,7,4'-trihydroxy-8-methoxyflavone, from the roots of *Scutellaria baicalensis* and enhancement of its activity by drug delivery system. *Antiviral Res.* 30: A1-A62 (1995); and Kitamura K et al. Baicalin, an inhibitor of HIV-1 production in vitro. *Antiviral Res.* 37: 131-140 (1998)], and baicalein has been shown to produce a hypotensive effect (Takizawa et al. Prostaglandin $I_2$ contributes to the vasodepressor effect of baicalein in hypertensive rats. *Hypertension* 31: 866-871(1998) and Chen Z Y et al. Endothelium-dependent contraction and direct relaxation induced by baicalein in rat mesenteric artery. *Eur J Pharmacol.* 374:41-47 (1999)]. More recently, baicalein has been implicated in the inhibition of expression of adhesion molecules induced by cytokines in human umbilical vein endothelial cells [Ikemoto, S et al. Antitumor effects of *Scutellariae radix* and its components baicalein, baicalin, and wogonin on bladder cancer cell lines. *Urology.* 55: 951-955 (2002); Middleton, E J and Kandaswani C. Effects of flavonoids on immune and inflammatory cell functions. *Biochem. Pharmacol.* 43: 1167-1179 (1992)].

Chart 1.
Bioactive flavonoids of *Scutellaria baicalensis* GEORGI.

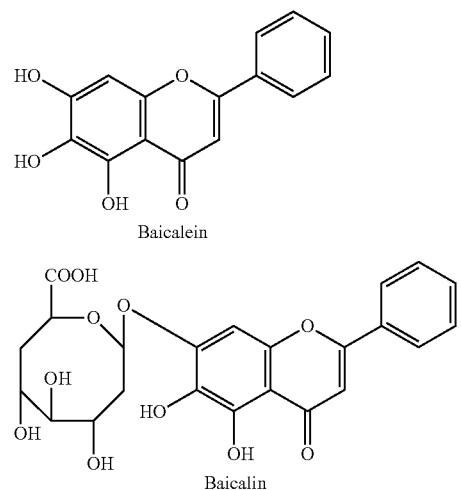

Baicalein

Baicalin

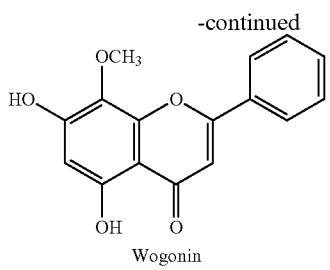

Wogonin

Current therapies for the treatment of septic shock include antibiotics, vasoconstrictors, steroids, and fluid supplementation to maintain the circulation volume; however, in many cases, these therapies have been deemed inefficient (Barron R L. Pathophysiology of septic shock and implications for therapy. *Clin. Pharm.* 12: 829-845 (1993)). It is desirable to provide compounds useful for the prevention or treatment of septic shock.

During the course of sepsis, nitric oxide (NO) is produced. Its metabolites impair normal vascular reactivity, in conjunction with elevated endotoxin levels. Inhibitors of NO synthase restore blood pressure, lower the cardiac index and increase pulmonary and systemic vascular resistance. Selective NOS inhibitors targeted against iNOS may prove to be beneficial. A small study with an inhibitor of NOS action, namely methylene blue, which inhibits the associated guanylyl cyclase enzyme, has indicated beneficial effects versus the cardiovascular parameters described above in patients with septic shock (Preiser, J C, Lejeune P, Roman A, et al. Methylene blue administration in septic shock: a clinical trial. Crit. Care Med., 23: 259-64(1995); Gachot B, Bedos J P, Veber B, et al. Short term effects of methylene blue on hemodynamics and gas exchange in humans with septic shock, Intensive Care Med 21:1027-31; Vincent, J L, Sun Q, Dubois, M-J, Clinical Trials of Immunomodulatory Therapies in Severe Sepsis and Septic Shock, CID, 34: 1084-1093 (2002)).

TNF-α (tissue necrosis factor), a cytokine that plays a critical role in eliciting the body's inflammatory response and is present in abnormally high levels in the joints of individuals suffering from rheumatoid arthritis, has been implicated as an immune modulator in the immune system. Inhibitors of TNF-α have been shown to halt the progression of cartilage destruction and relieve the symptoms of severe arthritis. Approximately 30% of moderate to severe arthritic patients are not responsive to these treatments (Feldman M, Maini R N, Discovery of TNF-α as a therapeutic target in rheumatoid arthritis: preclinical and clinical studies. *Joint Bone Spine* 2002, 69, 12-18; Lipsky P E, et al. Infliximab and methotrexate in the treatment of rheumatoid arthritis. *N. Engl. J. Med.* 2000, 343 1954-1602). Animal studies in association with studies conducted in humans indicate a potential role for TNF modulation in Crohn's disease, ulcerative colitis, insulin resistance, multiple sclerosis, multiple organ failure, pulmonary fibrosis, and atherosclerosis (Newton R C, Decicco C P, Therapeutic potential and strategies for inhibiting tumor necrosis factor-a. *J. Med. Chem.* 1999, 42, 2295-2314).

Aerobic organisms, which derive their energy from the reduction of oxygen, are susceptible to the damaging actions of the small amounts of $O_2-$, $OH$ and $H_2O_2$ that inevitably form during the metabolism of oxygen, especially in the reduction of oxygen by the electron transfer system of mitochondria. These three species, together with unstable intermediates in the peroxidation of lipids, are referred to as Reactive Oxygen Species (ROS). Many diseases such as, but not limited to, Alzheimer's Disease, Parkinson's disease, aging, cancer, myocardial infarction, atherosclerosis, autoimmune diseases, radiation injury, emphysema, sunburn, and joint disease (a. *Everything cytokine & beyond*, Cytokines Mini-Reviews, Chapter: Reactive Oxygen Species (ROS), Copyright 2003 ©R&D Systems; b. Channon K M, Guzik T J, Mechanisms of superoxide production in human blood vessels: relationship to endothelial dysfunction, clinical and genetic risk factors. *J. Physiol. Pharmacol.* 2002, 53(4), 515-524; c. Henrotin, Y E et al. The role of reactive oxygen species in homeostasis and degradation of cartilage. *OsteoArthritis and Cartilage* 2003, 11, 747-755; d. Arzimanoglou A et al. Epilepsy and neuroprotection: An illustrated review article. *Epileptic Disord* 2002, 3, 173-82; e. Seidman M D et al., Biologic activity of mitochondrial metabolites on aging and age-related hearing loss. *Am J Otol* 2000, 21(2):161-7.) are linked to damage from ROS as a result of an imbalance between radical-generating and radical-scavenging systems—a condition called oxidative stress. The discovery by McCord and Fridovich (McCord, J. M. & I. Fridovich *J. Biol. Chem.* 1969, 244:6049) of the superoxide dismutase (SOD) activity of erythrocuprein, together with the finding that almost all mammalian cells contain SOD, suggests a physiological role of at least the central ROS, superoxide.

SUMMARY OF THE INVENTION

When compared to conventional therapies described above, the present invention may provide a more useful therapy for the prevention or treatment of septic shock, organ damage and conditions and diseases associated with overproduction of TNF-α or overproduction of superoxide anion radical.

According to embodiments of the present invention, the present invention relates to a compound according to formula I:

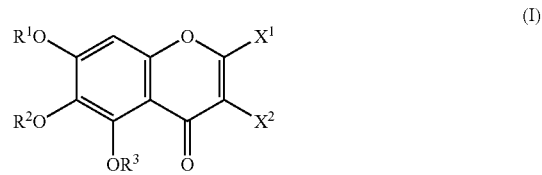

(I)

wherein:
$R^1$, $R^2$, and $R^3$ are each independently H, alkyl, alkenyl, alkynyl, —SO$_3$H, —PO$_3$H$_2$, or carbohydrate;
or $R^1$ and $R^2$ are each independently $(CH_2)_n Y$ and $[CH_2CH(OH)CH_2]Y$, wherein Y is H, OR$^4$, NR$^5$R$^6$, COOR$^4$, or OONR$^5$R$^6$ wherein R$^4$, R$^5$, and R$^6$ are each independently H, alkyl, alkenyl, alkynyl, or carbohydrate, and R$^5$ and R$^6$ together may form a 5 to 7-membered ring;
or $R^1$ and $R^2$ together are heterocycles;
or $R^2$ and $R^3$ together are heterocycles; and
$X^1$ and $X^2$ are each independently of the formula:

Ar—X$^3$-T wherein Ar may or may not be present and when Ar is present, Ar is phenyl, furanyl, thienyl, pyridyl, cyclohexyl or benzyl; wherein X$^3$ is H, C, N, NR', NR'R", NR'SO$_2$R", O, or S, subject to the proviso that the compound according to formula I is not baicalein or 5,6,7-trihydroxyisoflavone, wherein R' and R" are each independently H, alkyl, alkenyl, alkynyl, or carbohydrate;

wherein T is $(CH_2)_nY$ or $[CH_2CH(OH)CH_2]Y$, wherein Y is H, $OR^4$, $NR^5R^6$, $COOR^4$, or $OONR^5R^6$ wherein $R^4$, $R^5$, and $R^6$ are each independently H, alkyl, alkenyl, alkynyl, or carbohydrate; and $R^5$ and $R^6$ together may form a 5 to 7-membered ring; or pharmaceutically acceptable salts thereof.

According to other embodiments of the present invention, the invention relates to a method of preventing or treating conditions or diseases associated with overproduction of TNF-α, overproduction of superoxide anion radical, septic shock, inflammation, organ damage, neurodegenerative diseases, cancer, and cardiac disorders, comprising administering to a subject in need thereof, a pharmaceutical composition comprising a therapeutically effective amount of a compound of formula I described above.

According to still other embodiments, the present invention relates to a method of preventing or treating conditions or diseases associated with overproduction of TNF-α, overproduction of superoxide anion radical, organ damage, neurodegenerative diseases, cancer, and cardiac disorders, comprising administering to a subject in need thereof, a pharmaceutical composition comprising a therapeutically effective amount of a compound of the formula II:

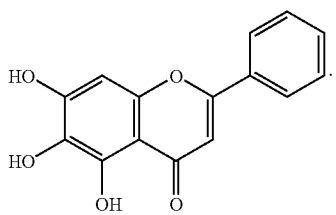

(II)

According to yet other embodiments, the present invention relates to a method of preventing or treating conditions or diseases associated with overproduction of TNF-α, overproduction of superoxide anion radical, organ damage, neurodegenerative diseases, cancer, and cardiac disorders, comprising administering to a subject in need thereof, a pharmaceutical composition comprising a therapeutically effective amount of a compound of the formula III:

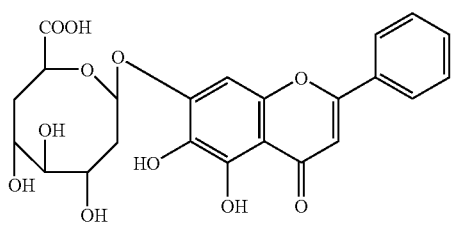

(III)

According to still other embodiment, the present invention relates to a method of preventing or treating conditions or diseases associated with overproduction of TNF-α, overproduction of superoxide anion radical, inflammation, organ damage, neurodegenerative diseases, cancer, and cardiac disorders, comprising administering to a subject in need thereof, a pharmaceutical composition comprising a therapeutically effective amount of a compound of the formula IV:

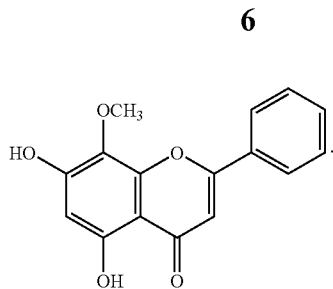

(IV)

According to yet other embodiments of the present invention, the present invention relates to a method of preventing or treating conditions or diseases associated with septic shock, overproduction of TNF-α, overproduction of superoxide anion radical, inflammation, organ damage, neurodegenerative diseases, cancer, and cardiac disorders, comprising administering to a subject in need thereof, a pharmaceutical composition comprising a therapeutically effective amount of a compound of the formula V:

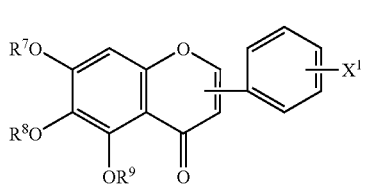

(V)

wherein:
$R^7$, $R^8$, and $R^9$ are each independently H, alkyl, —$SO_3H$, —$PO_3H_2$, carbohydrate, or benzyl;
or $R^7$ and $R^8$ together are heterocycles;
or $R^8$ and $R^9$ together are heterocycles;
$X^1$ is H, C, $NH_2$, $NHCOCH_3$, $NO_2$, or $OR^{10}$, wherein $R^{10}$ is H, alkyl, carbohydrate, or benzyl, or pharmaceutically acceptable salts thereof, with the proviso that when Ph-$X^1$ is at the 2-position and $R^7$, $R^8$, and $R^9$ are each independently H, alkyl or carbohydrate, the compound is not used to treat septic shock.

According to other embodiments of the present invention, the invention relates to a method of synthesizing the novel compounds described herein comprising reacting compounds described herein under suitable conditions as described herein to yield the desired compounds.

According to further embodiments, compounds of the present invention can be salt forms of the compound and moieties can be selected to confer water solubility to the compound(s).

BRIEF DESCRIPTION OF DRAWINGS

FIG. 1 illustrates effects of Compound 11a on the change in mean arterial blood pressure in lipopolysaccharide (LPS)-treated rats.

FIG. 2 illustrates effects of Compound 11a on the change in heart rate in LPS-treated rats.

FIG. 3 illustrates effects of Compound 11a on the plasma TNF-α level in LPS-treated rats.

FIG. 4 illustrates effects of Compound 11a on superoxide anion in LPS-treated rats.

FIG. 5 illustrates effects of Compound 11a on SGPT level in LPS-treated rats 8 hr after dosing.

FIG. 6 illustrates effects of Compound 11a on SGOT level in LPS-treated rats 8 hr after dosing.

FIG. 7 illustrates effects of baicalein on the plasma TNF-α level in LPS-treated rats.

FIG. 8 illustrates effects of baicalein on superoxide anion in LPS-treated rats.

FIG. 9 illustrates effects of Compound 11a on lung tissue in LPS-treated rats 8 hr after dosing.

DETAILED DESCRIPTION OF THE INVENTION

The present invention will now be described more fully hereinafter with reference to the accompanying figures, which further illustrate the invention described herein. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

All publications, patent applications, patents and other references cited herein are incorporated by reference in their entireties for the teachings relevant to the sentence and/or paragraph in which the reference is presented.

The term "alkyl" as used herein refers to C1-C20 inclusive, linear, branched, or cyclic, saturated or unsaturated hydrocarbon chains, including for example, methyl, ethyl, propyl, isopropyl, butyl, isobutyl, tert-butyl, pentyl, hexyl, octyl, ethenyl, propenyl, butenyl, pentyl, hexenyl, octenyl, butadienyl, and allenyl groups. Alkyl groups can either be unsubstituted or substituted with one or more non-interfering substituents, e.g., halogen, alkoxy, acyloxy, hydroxy, mercapto, carboxy, benzyloxy, phenyl, benzyl, or other functionality which has been suitably blocked with a protecting group so as to render the functionality non-interfering. Each substituent may be optionally substituted with additional non-interfering substituents. The term "non-interfering" characterizes the substituents as not adversely affecting any reactions to be performed in accordance with the process of this invention.

"Loweralkyl" as used herein refers to C1 to C4, C6 or C8 alkyl, which may be linear or branched and saturated or unsaturated.

"Cycloalkyl" is specified as such herein, and is typically C3, C4 or C5 to C6 or C8 cycloalkyl.

"Hydroxyalkyl" as used herein refers to C1 to C4 linear or branched hydroxy-substituted alkyl, i.e., —CH$_2$OH, —(CH$_2$)$_2$OH, etc.

"Aminoalkyl" as used herein refers to C1 to C4 linear or branched amino-substituted alkyl, wherein the term "amino" refers to the group NR'R", wherein R' and R" are independently selected from H or lower alkyl as defined above, i.e., —NH$_2$, —NHCH$_3$, —N(CH$_3$)$_2$, etc.

"Oxyalkyl" as used herein refers to C1 to C4 oxygen-substituted alkyl, i.e., —OCH$_3$, and the term "oxyaryl" as used herein refers to C3 to C10 oxygen-substituted cyclic aromatic groups.

"Alkenyl" refers to a hydrocarbon group, typically C2 to C4, derived from the corresponding alkyl and which contains at least one double bond (e.g., butadienyl). "Loweralkenyl" as used herein likewise refers to C1 to C4 alkenyl.

"Alkynyl" refers to a hydrocarbon group, typically C2 to C4, derived from the corresponding alkyl and which contains at least one triple bond (e.g., butadiynyl).

"Aryl" as used herein refers to C6 to C10 cyclic aromatic groups such as phenyl, naphthyl, and the like, and includes substituted aryl groups such as tolyl.

"Heterocycle" as used herein refers to a monovalent saturated, unsaturated, or aromatic carbocyclic group having a single ring or multiple condensed ring and having at least one hetero atom, such as N, O, or S, within the ring, which can optionally be unsubstituted or substituted with hydroxy, alkyl, alkoxy, halo, mercapto, and other non-interfering substituents. Examples of nitrogen heterocycles include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, and indoline.

"Halo" as used herein refers to any halogen group, such as chloro, fluoro, bromo, or iodo.

"Carbohydrate" as used herein refers to a compound which is either a carbohydrate per se made up of one or more monosaccharide units having at least 6 carbon atoms (which may be linear, branched or cyclic) with an oxygen atom bonded to each carbon atom; or a compound having as a part thereof a carbohydrate moiety made up of one or more monosaccharide units each having at least six carbon atoms (which may be linear, branched or cyclic), with an oxygen atom bonded to each carbon atom. Representative carbohydrates include the sugars (mono-, di-, tri-, and oligosaccharides), and polysaccharides such as starches, glycogen, cellulose and polysaccharide gums. Specific monosaccharides include C6 and above (preferably C6 to C8) sugars such as glucose, fructose, mannose, galactose, ribose, and sedoheptulose; di- and trisaccharides would include sugars having two or three monosaccharide units (preferably C5 to C8) such as sucrose, cellobiose, maltose, lactose, and raffinose.

"Flavonoids" or "bioflavonoids" as used herein relate to a ubiquitous group of polyphenolic substances which are present in most plants, concentrated in seeds, fruit skin or peel, bark, and flowers. Various classes of flavonoids include the following: flavanols, flavanones, flavones (2-phenylchromone), flavan-3-ols (catechins), anthocyanins, and isoflavones. Exemplary flavonoids include, but are not limited to, baicalein, baicalin, wogonin, and analogs thereof.

"Chromones" refer to benzo-γ-pyranones. Chromones represent the parent nucleus of flavones and isoflavones and are often components of plant pigments.

"Treat" or "treating" as used herein refers to any type of treatment that imparts a benefit to a patient afflicted with a disease, including improvement in the condition of the patient (e.g., in one or more symptoms), delay in the progression of the condition, prevention or delay of the onset of the disease, etc.

"Conditions," "diseases" and "disorders" are used interchangeably and refer to physiological states that can be prevented or treated by administration of the compounds of the present invention as described herein.

As, used herein, a "pharmaceutically acceptable" component (such as a salt, carrier, excipient or diluent) means that the compound or composition is suitable for administration to a subject to achieve the treatments described herein, without unduly deleterious side effects in light of the severity of the disease and necessity of the treatment.

"Therapeutically effective amount" as used herein refers to an amount necessary to prevent, delay or reduce the severity of the condition of interest and also includes an amount necessary to enhance normal physiological functioning.

In general, active compounds of the present invention comprise a structure according to the following formula:

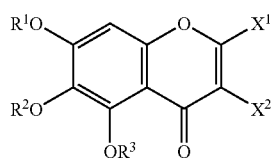

(I)

wherein:

$R^1$, $R^2$, and $R^3$ are each independently H, alkyl, alkenyl, alkynyl, —$SO_3H$, —$PO_3H_2$, or carbohydrate;

or $R^1$ and $R^2$ are each independently $(CH_2)_n Y$ and $[CH_2CH(OH)CH_2]Y$, wherein Y is H, $OR^4$, $NR^5R^6$, $COOR^4$, or $OONR^5R^6$ wherein $R^4$, $R^5$, and $R^6$ are each independently H, alkyl, alkenyl, alkynyl, or carbohydrate, and $R^5$ and $R^6$ together may form a 5 to 7-membered ring;

or $R^1$ and $R^2$ together are heterocycles;

or $R^2$ and $R^3$ together are heterocycles; and $X^1$ and $X^2$ are each independently of the formula:

$$Ar\text{—}X^3\text{-}T$$

wherein Ar may or may not be present and when Ar is present, Ar is phenyl, furanyl, thienyl, pyridyl, cyclohexyl or benzyl; wherein $X^3$ is H, C, N, NR', NR'R", NR'$SO_2$R", O, or S, subject to the proviso that the compound according to formula I is not baicalein or 5,6,7-trihydroxyisoflavone, wherein R' and R" are each independently H, alkyl, alkenyl, alkynyl, or carbohydrate; wherein T is $(CH_2)_n Y$ or $[CH_2CH(OH)CH_2]Y$, wherein Y is H, $OR^4$, $NR^5R^6$, $COOR^4$, or $OONR^5R^6$ wherein $R^4$, $R^5$, and $R^6$ are each independently H, alkyl, alkenyl, alkynyl, or carbohydrate, and $R^5$ and $R^6$ together may form a 5 to 7-membered ring; or pharmaceutically acceptable salts thereof.

The compound according to formula (I) can be water soluble. In some embodiments, $R^1$, $R^2$, and $R^3$ can be a moiety selected to confer water solubility to the compound to provide a novel, water-soluble compound. In addition to the description above, $R^1$, $R^2$, and $R^3$ can be a sulphate ($SO_3H$), sulphonate, phosphate ($PO_3H_2$) or phosphonate as selected to provide a novel, water-soluble compound. Moreover, the sulphate, sulphonate, phosphate, or phosphonate can be in the form of a water-soluble salt. As a representative non-limiting example, a water-soluble salt can be formed using an alkali metal salt, such as sodium, potassium, or ammonium. The water-soluble salt may be in the form of a mono, di-, or tri-alkali metal salt.

Active compounds of the present invention further comprise a structure according to the following formulas:

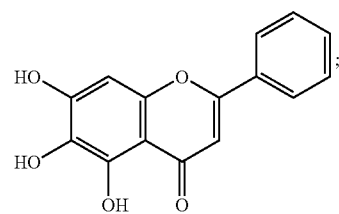

(II)

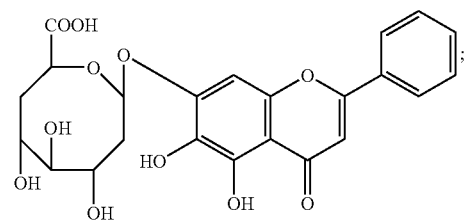

(III)

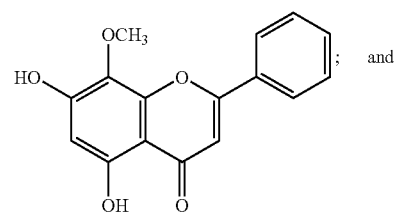

(IV)

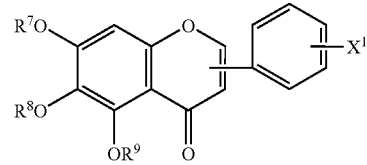

(V)

wherein:

$R^7$, $R^8$, and $R^9$ are each independently H, alkyl, —$SO_3H$, —$PO_3H_2$, carbohydrate, or benzyl;

or $R^7$ and $R^8$ together are heterocycles;

or $R^8$ and $R^9$ together are heterocycles;

$X^1$ is H, C, $NH_2$, $NHCOCH_3$, $NO_2$, or $OR^{10}$, wherein $R^{10}$ is H, alkyl, carbohydrate, or benzyl, or pharmaceutically acceptable salts thereof, wherein $X^1$ can be attached in either an ortho, meta or para relationship, with the proviso that when Ph-$X^1$ is at the 2-position, the compound is not used to treat septic shock.

$R^7$, $R^8$, and $R^9$ can be a moiety selected to confer water solubility to the compound to provide a novel, water-soluble compound. In addition to the description above, $R^7$, $R^8$, and $R^9$ can be a sulphate ($SO_3H$), sulphonate, phosphate ($PO_3H_2$), or phosphonate as selected to provide a novel, water-soluble compound. Moreover, the sulphate, sulphonate, phosphate, or phosphonate can be in the form of a water-soluble salt. As a representative non-limiting example, a water-soluble salt can be formed using an alkali metal salt, such as sodium, potassium, or ammonium. The water-soluble salt may be in the form of a mono, di-, or tri-alkali metal salt.

Active compounds of the present invention further comprise known water-soluble derivatives of baicalein including, but not limited to, baicalein-6-sulfate, baicalein-6,7 disulfate, bacalein-6-phosphate, baicalein-6,7-diphosphate, bacalein-5,6,7-triphosphate, and pharmaceutically acceptable salts thereof, as disclosed in Nagai H, et al. Inhibition of hypersensitivity reactions by soluble derivatives of baicalein. *Jpn J Pharmacol December;* 25(6):763-7 (1975); Nohara, A. et al. Takeda Kenkyushoho 30(4): 677-81(1971); and U.S. Pat. No. 3,549,662.

A. Synthesis of Novel Compounds

Variations on the following general synthetic methods will be readily apparent to those skilled in the art and are deemed to be within the scope of the present invention.

Scheme 1:
General Sythesis of Flavone Analogs

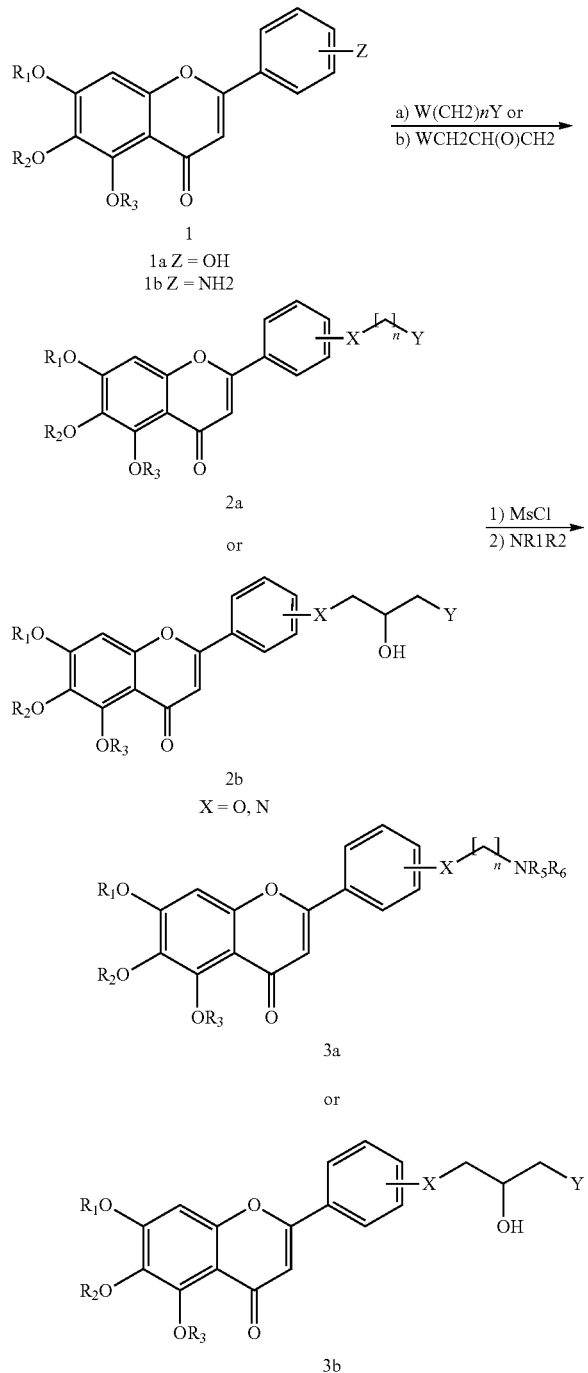

Scheme 1 illustrates the general synthesis of 4'-amino- and 4'-oxy derivatives of baicalein. Baicalein analogs (1) were synthesized as shown in Schemes 2 and 3. Alkylation of baicalein analogs (1) in the presence of a base (e.g., $K_2CO_3$) or tertiary amine (e.g., $Et_3N$) with an electrophile such as W(CH2)nY, wherein Y is defined as above, W(CH2)nOR, W(CH2)nCO$_2$R or W(CH2)nCONR$_1$R$_2$ wherein W is a leaving group, and R, R$_1$ and R$_2$ are as defined previously, WCH2CH(O)CH2 or HOCH$_2$CH(O)CH$_2$ provided baicalein derivatives (2a and 2b, respectively). Alkylated product (2) wherein Y is OH is treated with MsCl followed by an amine to provide baicalein analogs as shown in (3).

Scheme 2:
Sythesis of 4'-oxybaicalein derivatives

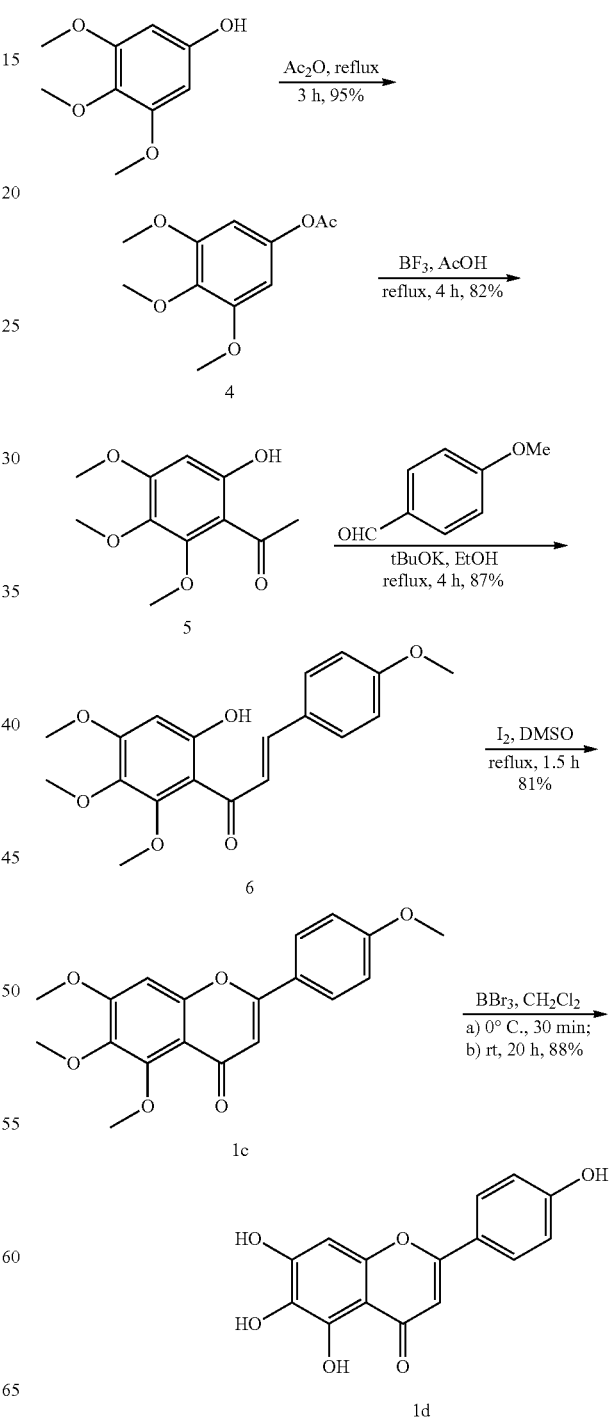

Scheme 3:
Synthesis of 4'-aminobaicalein derivatives

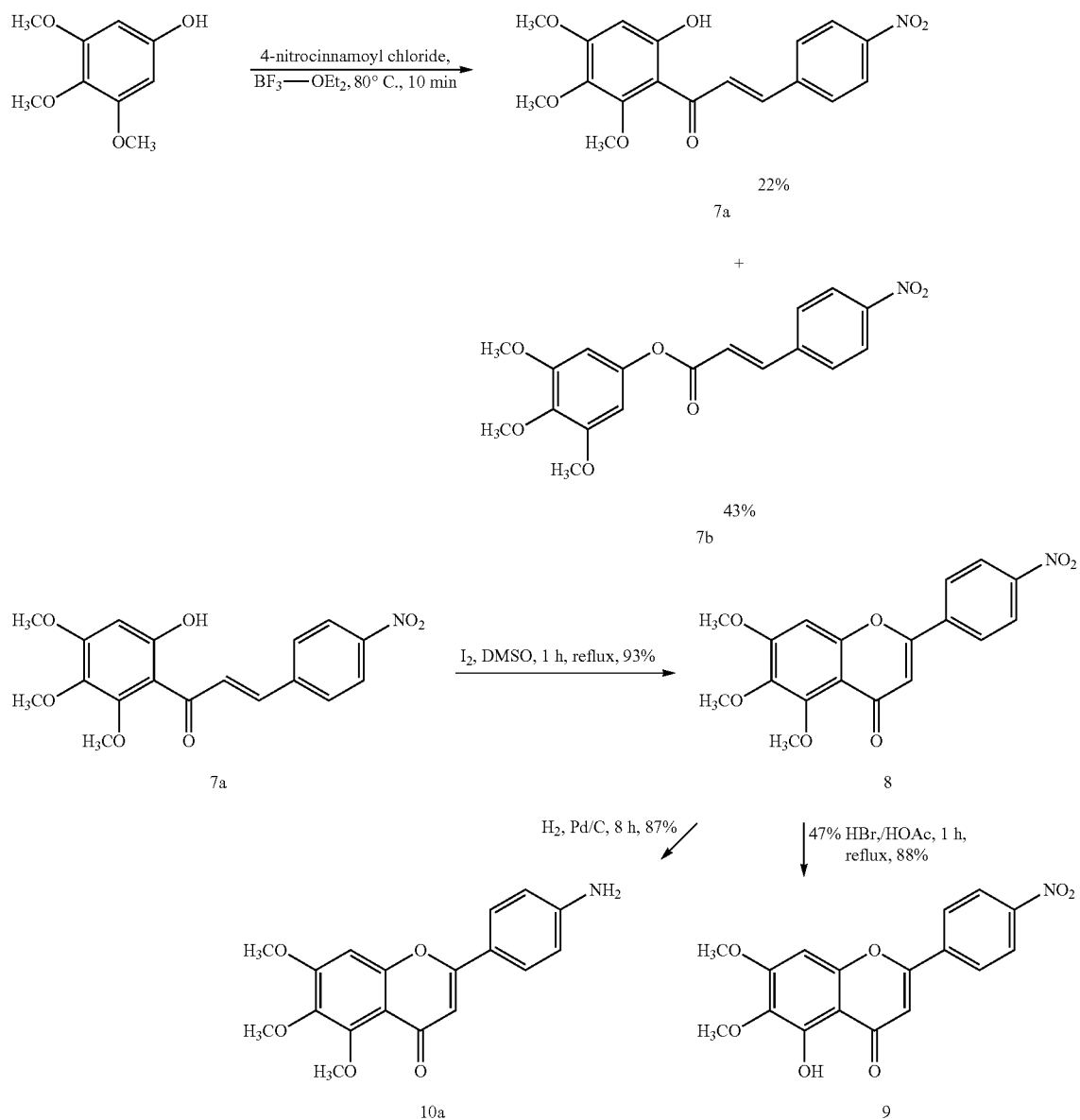

Additional compounds and synthetic methods can be found in U.S. Pat. No. 4,495,198 to Wu; U.S. Pat. No. 4,797,498 to Albrecht et al.; U.S. Pat. No. 4,758,679 to Schmitthenner et al.; U.S. Pat. No. 4,668,805 to Wu; U.S. Pat. No. 4,668,804 to Wu; U.S. Pat. No. 4,495,198 to Wu; WO 01/30342 to Lee et al.; Suk K. et al Flavonoid Baicalein Attenuates Activation-Induced Cell Death of Brain Microglia. *J. Pharmacol. Exp. Therap.* 2003, 305, 638-645; Riseman, J E F et al. *Am. J. Cardiol.* 1965, 15, 220; and Wu, E S C et al. Flavones. 3. Synthesis, Biological Activities, and Conformational Analysis of Isoflavone Derivatives and Related Compounds. *J. Med. Chem.* 1992, 35, 3519-3525.

B. Pharmaceutically Acceptable Salts

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. In particular embodiments, pharmaceutically acceptable salts are formed with hydrochloric acid. In other particular embodiments, pharmaceutically acceptable salts are formed with malic acid.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

C. Pharmaceutical Formulations

The flavonoids and flavonoid analogs of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

It will be appreciated that certain compounds of the above Formulae can possess an asymmetric carbon atom(s) and are thus capable of existing as enantiomers. Unless otherwise specified, this invention includes such enantiomers, including racemates. The separate enantiomers may be synthesized from chiral starting materials, or the racemates can be resolved by procedures that are well known in the art of chemistry such as chiral chromatography, fractional crystallization of diastereometric salts and the like.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. In one particular embodiment, a pharmaceutical composition comprises less than 80% by weight of active compound. In other particular embodiments, a pharmaceutical composition comprises less than 50% by weight of active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, tablets, dragees, or syrups each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3(6):318 (1986)) and typically take the form of an optionally buffered aqueous solution of the active compound. Suitable formulations comprise citrate or bis\tris buffer (pH 6) or ethanol/water and contain from 0.01 to 0.2M active ingredient.

The present invention may also be formulated into a sustained-release preparation. A sustained-release composition includes, but is not limited to, those in which the active ingredient is bound to an ion exchange resin which is optionally coated with a diffusion barrier to modify the release properties of the resin.

Carriers and/or diluents which may be used include vaseline, lanoline, glycerin, vegetable oils, or fat emulsions, polyethylene glycols, alcohols, transdermal enhancers, natural or hardened oils or waxes, and combinations of two or more thereof.

In particular embodiments, the present invention provides compounds of the formulas described herein that are water soluble. In some embodiments, water solubility is conferred to the compounds described herein by preparation of a water-soluble salt thereof. As a non-limiting example, alkali metal salts such as sodium, potassium, or ammonium can be used to confer water solubility to the compounds. The water-soluble salt may be in the form of a mono, di-, or tri-alkali metal salt.

In some embodiments, a moiety capable of conferring water solubility to the compound to provide a novel, water-soluble compound can be added. Such moieties include, but are not limited to, sulphate, sulphonate, phosphate, or phosphonate moieties as selected to provide a novel, water-soluble compound. Moreover, the sulphate, sulphonate, phosphate, or phosphonate can be in the form of a water-soluble salt as described above. In some embodiments, the moiety capable of conferring water solubility to the compound can be $SO_3H$ or $PO_3H_2$ and salts thereof, including, but not limited to, sodium and potassium. In some embodiments, the active compounds of the present invention comprise known water-soluble derivatives of baicalein including, but not limited to, baicalein-6-sulfate, baicalein-6,7-disulfate, bacalein-6-phosphate, bacalein-6,7-diphosphate, bacalein-5,6,7-triphosphate, and pharmaceutically acceptable salts thereof.

D. Methods of Use

In addition to the compounds of the formulas described herein, the present invention also provides useful therapeutic methods. For example, the present invention provides a method of preventing or treating conditions or diseases associated with overproduction of TNF-α, overproduction of superoxide anion radical, septic shock, inflammation, organ damage, neurodegenerative diseases, cancer, and cardiac disorders.

In particular embodiments, conditions or diseases associated with overproduction of TNF-α include, but are not limited to, arthritis, rheumatoid arthritis, Crohn's disease, ulcerative colitis, insulin resistance, multiple sclerosis, organ failure, pulmonary fibrosis, and atherosclerosis.

In particular embodiments, conditions or diseases associated with overproduction of superoxide anion radical include, but are not limited to, Alzheimer's disease, Parkinson's disease, aging, cancer, myocardial infarction, atherosclerosis, autoimmune disease, radiation injury, emphysema, sunburn, joint disease, and oxidative stress.

In particular embodiments, organ damage includes, but is not limited to, liver damage, kidney damage, and lung damage. Additionally, organ damage may result from causes which include, but are not limited to, cancer, infections, exposure to environmental toxins or allergens, exposure to chemical substances such as drugs (recreational or therapeutic) and alcohol, and conditions such as hepatitis, cirrhosis, diabetes, hypertension, glomerulonephritis, kidney stones, polycystic kidney disease, pneumonia, tuberculosis, emphysema, bronchitis, and asthma.

In particular embodiments, neurodegenerative diseases include, but are not limited to, Parkinson's disease, Alzheimer's disease, cognition deficit, memory loss, and stroke.

In other particular embodiments, exemplary cancers include, but are not limited to, leukemia, lymphoma, colon cancer, renal cancer, liver cancer, breast cancer, lung cancer, prostate cancer, ovarian cancer, melanoma, small cell lung cancer, testicular cancer, esophageal cancer, stomach cancer, endometrial cancer, central nervous system cancer, and the like. The term "cancer" has its understood meaning in the art, for example, an uncontrolled growth of tissue that has the potential to spread to distant sites of the body (i.e., metastasize). Preferred are methods of treating and preventing tumor-forming cancers. The term "tumor" is also understood in the art, for example, as an abnormal mass of undifferentiated cells within a multicellular organism. Tumors can be malignant or benign. Preferably, the inventive compounds and methods disclosed herein are used to prevent and treat malignant tumors.

In still yet other particular embodiments, cardiac disorders include, but are not limited to, cardiac ischemia, congestive heart failure, and hypertension.

Suitable subjects to be treated according to the present invention include both avian and mammalian subjects, preferably mammalian. Mammals according to the present invention include but are not limited to canine, felines, bovines, caprines, equines, ovines, porcines, rodents (e.g. rats and mice), lagomorphs, primates, and the like, and encompass mammals in utero. Humans are preferred.

Illustrative avians according to the present invention include chickens, ducks, turkeys, geese, quail, pheasant, ratites (e.g., ostrich) and domesticated birds (e.g., parrots and canaries), and include birds in ovo. Chickens and turkeys are preferred.

Any mammalian subject in need of being treated according to the present invention is suitable. Human subjects are preferred. Human subjects of both genders and at any stage of development (i.e., neonate, infant, juvenile, adolescent, adult) can be treated according to the present invention.

As noted above, the present invention provides pharmaceutical formulations comprising the compounds of formulae described herein, or pharmaceutically acceptable salts thereof, in pharmaceutically acceptable carriers for any suitable route of administration, including but not limited to, oral, rectal, topical, buccal, parenteral, intramuscular, intradermal, intravenous, and transdermal administration.

According to the present invention, methods of this invention comprise administering an effective amount of a composition of the present invention as described above to the subject. The effective amount of the composition, the use of which is in the scope of present invention, will vary somewhat from subject to subject, and will depend upon factors such as the age and condition of the subject and the route of delivery. Such dosages can be determined in accordance with routine pharmacological procedures known to those skilled in the art. For example, the compounds of the present invention can be administered to the subject in an amount ranging from a lower limit from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, or 10% to an upper limit ranging from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% by weight of the composition. In some embodiments, the compounds comprise from about 0.05 to about 95% by weight of the composition. In other embodiments, the compounds comprise from about 0.05 to about 60% by weight of the composition. In still other embodiments, the compounds comprise from about 0.05 to about 10% by weight of the composition.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

In particular embodiments, compounds of the present invention may be administered at a daily dosage of from about 0.1 mg to about 20 mg per kg of animal body weight, which can be given in divided doses q.d. to q.i.d. or in a sustained release form. For humans, the total daily dose may be in the range of from about 5 mg to about 1,400 mg, and in other particular embodiments, the total daily dose is in the range of from about 10 mg to about 100 mg. In still other embodiments, the unit dosage forms suitable for oral administration may comprise about 2 mg to about 1,400 mg of the compound optionally admixed with a solid or liquid pharmaceutical carrier or diluent.

In particular embodiments, active compounds of the present invention can be administered alone or in combination with other therapeutic agents. For example, active compounds of the present invention can be coadministered with other compounds of the present invention and compounds now known, or later identified, to be useful for the prevention or treatment of conditions or diseases associated with overproduction of TNF-α, overproduction of superoxide anion radical, septic shock, inflammation, organ damage, neurodegenerative diseases, cancer, and cardiac disorders. Exemplary compounds include, but are not limited to, antibiotics, antimicrobials, antivirals, vaccines, and the like.

In general, the compounds of the present invention can be administered in any amount appropriate to administer to the subject for treatment of the condition desired to be treated as determined by one of ordinary skill in the art by reference to the pertinent texts and literature and/or by using routine experimentation. (See, for example, Remington, *The Science And Practice of Pharmacy* (9th Ed. 1995).

The present invention is explained in greater detail in the following non-limiting examples.

EXAMPLE 1

Preparation of Novel Baicalein Analogs

Preparation of 3,4,5-Trimethoxyphenyl acetate (4). A solution of 3,4,5-trimethoxyphenol (5.52 g, 30 mmol) in acetic anhydride (15 mL) was refluxed for 4 h. The reaction mixture was poured onto crushed ice (50 g). The resulting precipitate was collected and washed with water. The residue was dried in vacuum at 50° C. for 24 h to afford white crystals (6.31 g, 93%), 74-75° C.; $^1$H NMR (CDCl$_3$, 200 M Hz) δ 6.34 (s, 2H), 3.83 (s, 6H), 3.82 (s, 3H), 2.29 (s, 3H); $^{13}$C NMR (CDCl$_3$, 50 M Hz) δ 169.6 (s), 153.5 (s, 2C), 146.7 (s), 135.8 (s), 99.1 (d, 2C), 60.9 (q), 56.1 (q, 2C), 21.1 (q).

Preparation of 1-(6-Hydroxy-2,3,4,-trimethoxyphenyl) ethanone (5). Boron trifluoride etherate (13.0 mL) was added dropwise to a solution of 3,4,5-tri-methoxyphenyl acetate 4 (6.78 g, 30 mmol) in glacial acetic acid (10 mL). The mixture was stirred at 70° C. for 2 h. Then the mixture was poured onto crushed ice (80 g). The light brown oil was separated and distilled under reduced pressure to furnish light yellow oil (5.56 g, 82%); $^1$H NMR (CDCl$_3$, 200 M Hz) δ 13.42 (br s, 1H), 6.23 (s, 3H), 3.82 (s, 3H), 3.99 (s, 3H), 3.88 (s, 3H), 3.79 (s, 3H), 2.65 (s, 3H); $^{13}$C NMR (CDCl$_3$, 50 M Hz) δ 203.3 (s), 161.8 (s), 160.0 (s), 155.2 (s), 134.7 (s), 108.4 (s), 96.0 (d), 60.9 (q, 2C), 56.0 (q, 3H), 31.8 (q).

Preparation of 6-hydroxy-1-(4-methoxycinnamoyl)-2,3,4-Trimethoxy-benzene (6). To a solution of 1-(6-hydroxy-2,3, 4,-Trimethoxyphenyl)ethanone 5 (2.26 g, 10 mmol), 4-methoxybenzaldehyde (1.63 g, 12 mmol) and t-BuOK (2.11 g, 22 mmol) in ethanol (30 mL) was refluxed for 4 h. The reaction mixture was poured onto crushed ice (100 g). The resulting precipitate was filtered and washed with water. The residue was air-dried at room temperature. The crude product was recrystallized from ethyl acetate to afford chalcone as orange crystals (2.99 g, 87%): $^1$H NMR (CDCl$_3$, 200 M Hz) δ 11.75 (br s, 1H), 7.84 (s, 2H), 7.60 (d, J=8.8 Hz, 2H), 6.93 (d, J=8.8 Hz, 2H), 6.29 (s 1H), 3.93 (s 3H), 3.90 (s, 3 M), 3.85 (s, 3H), 3.84 (s, 3H); $^{13}$C NMR (CDCl$_3$, 50 M Hz) δ 192.7 (s), 162.6 (s), 161.5 (s), 159.9 (s), 154.9 (s), 143.3 (d), 135.2 (s), 130.1 (d, 2C), 128.0 (s), 124.0 (d), 114.4 (d, 2C), 108.7 (s), 96.5 (d), 61.8 (q), 61.2 (q), 56.0 (q), 55.3 (q).

Preparation of 4',5,6,7-Tetramethoxyflavone (1c). A solution of the chalcone 6 (1.72 g, 5 mmol) and iodine (catalytic amount) in dimethyl sulfoxide (6 mL) was refluxed for 30 min, and then the reaction mixture was poured onto crushed ice (50 g). The resulting precipitate was collected and washed with 5% sodium thiosulfate solution (30 mL) and water. Recrystallization from ethanol afforded the title flavone (1.38 g, 81%) as bright yellow crystals: $^1$H NMR (CDCl$_3$, 200 M Hz) δ 7.81 (d, J=9.0 Hz, 2H), 6.98 (d, J=9.0 Hz, 2H), 6.79 (s 1H), 6.57 (s, 1H), 3.99 (s 3H), 3.98 (s, 3H), 3.92 (s, 3H), 3.87 (s, 3H); $^{13}$C NMR (CDCl$_3$, 50 M Hz) δ 177.1 (s), 162.0 (s), 161.0 (s), 157.5 (s), 154.3 (s), 152.4 (s), 140.2 (s), 127.5 (d, 2C), 123.6 (s), 114.2 (d, 2C), 122.7 (s), 106.8 (d), 96.1 (d), 62.0 (q), 61.4 (q), 56.1 (q), 55.3 (q).

Preparation of 4',5,6,7-Tetrahydroxyflavone (Id). Boron tribromide (0.7 mL) was added dropwise to a solution of the flavone 1c (68.4 mg, 0.2 mmol) in dichloromethane (3 mL) at 0° C. The mixture was allowed to warm to room temperature after 30 min and stirred at room temperature for 20 h. Then the mixture was poured into ice water (20 mL). The organic layer was separated and concentrated under reduce pressure. The aqueous layer was poured onto the organic residue. After stirring, the precipitate was filtered off and washed with water. Recrystallization from ethanol afforded the title compound (50 mg, 88%) as yellow crystals: $^1$H NMR (DMSO, 200 M Hz) δ 10.20 (br s, 2H), 7.90 (d, J=8.7 Hz, 2H), 6.90 (d, J=8.7 Hz, 2H), 6.72 (s 1H), 6.57 (s 1H), 3.75 (br s, 2H)); $^{13}$C NMR (DMSO, 50 M Hz) δ 182.1 (s), 163.6 (s), 161.0 (s), 153.3 (s), 149.7 (s), 147.1 (s), 129.2 (s), 128.4 (d, 2C), 121.5 (s), 116.0 (d, 2C), 104.1 (s), 102.3 (d), 93.9 (d).

Preparation of 7-Methoxy-4',5,6-trihydroxyflavone (1f). Similar to the preparation of 1c, 1e (4'-benzyloxy-5,6,7-trimethoxyflavone) was prepared from 6-hydroxy-1-(4-benzyloxycinnamoyl)-2,3,4-trimethoxybenzene (6b), which, in turn, was obtained from the reaction of the acetophenone 5 and 4-benzyloxybenzaldehyde. A solution of 1e (500 mg, 1.20 mmol) in 48% HBr (5 mL) and glacial acetic acid (10 mL) was refluxed for 2 h. Then, the reaction mixture was poured onto crushed ice (ca. 100 g). The resulting precipitate was filtered and washed with water. Recrystallization from ethanol furnished compound 1f (305 mg, 85%). $^1$H NMR (DMSO, 200 M Hz) δ 12.63 (br s, 1H), 10.30 (br s, 1H), 8.70 (br s, 1H), 7.93 (d, J=8.8 Hz, 2H), 6.92 (d, J=8.8 Hz, 2H), 6.88 (s 1H), 6.78 (s 1H), 3.90 (s, 3H); $^{13}$C NMR (DMSO, 50 M Hz) δ 182.2 (s), 163.8 (s), 161.1 (s), 154.3 (s), 149.6 (s), 146.2 (s), 129.9 (s), 128.4 (d, 2C), 121.4 (s), 116.0 (d, 2C), 105.0 (s), 102.5 (d), 91.1 (d), 56.3 (q). The stereochemistry of compound 1f was confirmed by cosy and nosy experiments.

Preparation of 4',7-Methoxy-5,6-dihydroxyflavone (1g). Similar to the preparation of 1f, the title compound (407 mg) was prepared from 1c (500 mg, 1.46 mmol) in 89% yield. $^1$H NMR (DMSO, 200 M Hz) δ 12.59 (br s, 1H), 8.70 (br s, 1H), 8.02 (d, J=8.6 Hz, 2H), 7.08 (d, J=8.6 Hz, 2H), 6.90 (s 1H), 6.85 (s 1H), 3.91 (s, 3H), 3.84 (s, 3H); $^{13}$C NMR (DMSO, 50 M Hz) δ 182.2 (s), 163.3 (s), 161.3 (s), 154.4 (s), 149.7 (s), 146.2 (s), 130.0 (s), 128.2 (d, 2C), 123.0 (s), 114.6 (d, 2C), 105.1 (s), 103.1 (d), 91.2 (d), 56.3 (q), 55.6 (q). The stereochemistry of compound 1g was confirmed by cosy and nosy experiments.

Preparation of 4'-hydroxy-5,6,7-trimethoxyflavone (1h). To a suspension of 1e 4'-benzyloxy-5,6,7-trimethoxyflavone, (120 mg, 0.29 mmol) and a catalytic amount of palladium on charcoal (10%) in ethanol (15 mL) was hydrogenated at atmospheric pressure for 4 h. The catalyst was filtered off and the solvent was stripped off to produce the title compound 1h (89 mg, 95%) as slight yellow crystals. Without purification, the purity of this compound is higher than 95%. $^1$H NMR (DMSO, 200 MHz), δ 7.88 (d, J=8.6 Hz, 2H), 7.16 (s, 1H), 6.90 (d, J=8.6 Hz, 2H), 6.60 (s, 1H), 3.93 (s 3H), 3.93 (s, 3H), 3.78 (s, 3H), 3.75 (s, 3H).

Preparation of 2'-Hydroxy-4',5',6'-trimethoxy-4-nitrochalcone (7a). A mixture of 3,4,5-trimethoxyphenol (1.85 g, 10 mmol) and 4-nitrocinnamoyl chloride (2.11 g, 10 mmol) was dissolved in BF$_3$-Et$_2$O complex (10 ml) and heated to 80° C. for 10 min, and then quenched with excess of water. The aqueous layer was extracted with dichloromethane. The combined organic layer was concentrated and the residue was purified by column chromatography on silica gel (CH$_2$Cl$_2$: EtOAc:Hexane=1:1:3) gave 7a (0.79 g, 22%) and 7b (1.54 g, 43%). $^1$H NMR (400 MHz, CDCl$_3$) μ 3.81 (s, 3H), 3.90 (s, 3H), 3.91 (s, 3H), 6.29 (s, 1H), 7.74 (d, J=8.8 Hz, 2H), 7.76 (d, J=16.0 Hz, 1H), 8.01 (d, J=16.0 Hz, 1H), 8.26 (d, J=8.8 Hz, 2H), 13.44 (s, 1H).

Preparation of 5,6,7-trimethoxy-4'-nitroflavone (8). A mixture of 7a (0.80 g, 2.2 mmol) and iodine (20 mg) in DMSO (5 ml) was refluxed for 1 h, and then carefully poured onto crushed ice. The precipitate was filtered and washed with 20% Na$_2$SO$_3$. Recrystallization of the precipitate from acetone afforded 8 (0.73 g, 93%). $^1$H NMR (400 MHz, CDCl$_3$) δ 3.91 (s, 3H), 3.97 (s, 3H), 3.98 (s, 3H), 6.74 (s, 1H), 6.82 (s, 1H), 8.03 (d, J=8.8 Hz, 2H), 8.34 (d, J=8.8 Hz, 2H).

Preparation of 6,7-dimethoxy-5-hydroxy-4'-nitro-flavone (9a). A solution of 8 (0.11 g, 0.32 mmol) in 47% HBr (2.5 ml) and glacial acetic acid (5 ml) was refluxed for 1 h, and then poured onto crushed ice. The precipitate was filtered and recrystallized from ethanol to afford 9 (0.09 g, 88%). $^1$H NMR (400 MHz, CDCl$_3$) δ 3.91 (s, 3H), 3.98 (s, 3H), 6.58 (s, 1H), 6.75 (s, 1H), 8.05 (d, J=8.8 Hz, 2H), 8.36 (d, J=8.8 Hz, 2H).

Preparation of 5,7-dihydroxy-6-methoxy-4'-nitroflavone (9b). To a solution of 8 (71 mg, 0.2 mmol) in CH$_2$Cl$_2$ (5 mL) was added a 1M solution of boron tribromide (0.4 mL, 0.4 mmol) in CH$_2$Cl$_2$ at −78° C. The solution was stirred for an additional 2 h and at −20° C. for 5 h then quenched with water (10 mL). The precipitate was collected by filtration and recrystallized from CH$_2$Cl$_2$ to afford crude product 5 (30 mg, 46%). $^1$H NMR (400 MHz, DMSO) δ 3.93 (s, 3H), 7.01 (s, 1H), 7.21 (s, 1H), 8.38-8.39 (m, 4H).

Preparation of 4'-amino-5,6,7-trimethoxyflavone (10a). A solution of the flavone 8 (0.07 g, 0.2 mmol) in dioxane (10 ml) was hydrogenated at 40 psi in the presence of 5% palladium on charcoal (20 mg) for 8 h and the catalyst was filtered off. Dioxane was removed from the filtrate under reduced pressure to give 10a (0.05 g, 87%). $^1$H NMR (400 MHz, CDCl$_3$) δ 3.98 (s, 3H), 3.94 (s, 3M), 3.95 (s, 3H), 6.45 (s, 1H), 6.71 (d, J=8.8 Hz, 2H), 6.75 (s, 1H), 7.65 (d, J=8.8 Hz, 2H).

Preparation of 4'-amino-5,7-dihydroxy-6-methoxyflavone (10b): To a solution of the flavone 10a (130 mg, 0.4 mmol) in CH$_2$Cl$_2$ (10 mL) was added a 1M solution of boron tribromide (1.5 mL, 1.5 mmol) in CH$_2$Cl$_2$ at −78° C. The solution was stirred for an additional 2 h and at −20° C. for 5 h, then quenched with water (10 mL). The precipitate was collected by filtration to give crude product 10b (51 mg, 43%). $^1$H NMR (400 MHz, DMSO) δ 3.89 (s, 3H), 6.68 (s, 1H), 6.74 (d, J=8.8 Hz, 2H), 6.87 (s, 1H), 7.82 (d, J=8.8 Hz, 2H).

Preparation of 4'-(N,N-dimethylamino)-5,6,7-trimethoxyflavone (10c) and 4'-(methylamino)-5,6,7-trimethoxyflavone (10d). A mixture of the aminoflavone 10a (0.54 g, 1.65 mmol), anhydrous potassium carbonate (0.91 g, 6.6 mmol) and iodomethane (0.2 mL, 3.3 mmol) in acetone (20 mL) was stirred for 48 h, then acetone was removed. The residue was extracted with methylene chloride and purification by column chromatography on silica gel (acetone:toluene=1:5) to give 7 (0.22 g, 38%), 10d (0.26 g, 46%) and recover 10a (65 mg, 12%). 10c: $^1$H NMR (400 MHz, CDCl$_3$) δ 3.04 (s, 6H), 3.89 (s, 3H), 3.95 (s, 3H), 3.96 (s, 3H), 6.52 (s, 1H), 6.72 (d, J=8.8 Hz, 2H), 6.76 (s, 1H), 7.73 (d, J=8.8 Hz, 2H). 10d: $^1$H NMR (400 MHz, Acetone) δ 2.82 (d, J=13.6 Hz, 3H), 3.80 (s, 3H), 3.86 (s, 3H), 3.99 (s, 3H), 6.41 (s, 1H), 6.72 (d, J=8.8 Hz, 2H), 7.06 (s, 1H), 7.79 (d, J=8.8 Hz, 2H).

Preparation of 4'-(methylsulfonamido)-5,6,7-trimethoxyflavone (10e). The aminoflavone 10a (0.13 g, 0.40 mmol) was dissolved in 5 mL of dry methylene chloride, then 2 mL of freshly distilled pyridine was added. The solution was cooled to 0° C. then was dropwise added freshly distilled methanesulfonyl chloride (0.6 mmol). The reaction mixture was stirred at 0° C. for 1 h and at room temperature for an additional hour, then poured into 30 mL saturated NaHCO$_3$. The resulting mixture was extracted with methylene chloride. The combined organic layers were washed with 5% HCl to remove pyridine, dried over Na$_2$SO$_4$ and concentrated. The residue was purified by column chromatography on silica gel (acetone:toluene=1:5) to give 10e (0.12 g, 74%). $^1$H NMR (400 MHz, Acetone) δ 3.11 (s, 3H), 3.81 (s, 3H), 3.87 (s, 3H), 4.00 (s, 3H), 6.60 (s, 1H), 7.11 (s, 1H), 7.50 (d, J=8.8 Hz, 2H), 8.02 (d, J=8.8 Hz, 2H).

Preparation of sodium baicalein-6-sulfate (11a). To a solution of baicalein (300 mg, 1.11 mmol) in DMF (0.4 mL) and tetrahydrofuran (5 mL) was added sulfur trioxide trimethylamine complex (310 mg, 2.23 mmol). The reaction mixture was stirred at room temperature for 4 h. Then the reaction mixture was poured onto crushed ice (ca. 100 g). The resulting precipitate was filtered and washed with water. The precipitates were suspended in water (10 mL), followed by addition of Na-type of Amberlite IR-120 cation exchange resins (3 g). The mixture was heated to 50° C. and maintained this temperature for 5 h to dissolve the precipitates. The resins were filtered off and the filtrate was concentrated to dryness. The residue was solidified by adding absolute ethanol (3 mL). The solid was filtered and washed with ether to afforded the title compound (390 mg, 85%).

Preparation of disodium baicalein-6-phosphate (11b). The product was prepared from baicalein using the method as described in U.S. Pat. No. 3,549,662.

Preparation of 4'-(Carbmethoxymetboxy)-5,6,7-trimethoxyflavone (12a). To a suspension of 1h (100 mg, 0.30 mmol), methyl bromoacetate (150 mg, 1.0 mol), potassium carbonate (300 mg), and potassium iodide (200 mg) in acetone (15 mL) was refluxed for 5 h. Then the reaction mixture was concentrated. The residue was added water and extracted with ethyl acetate. The combined organic layers were washed with brine, dried, filtered, and concentrated. The residue was purified by a silica column (ethyl acetate/n-hexane=2:1) to afford compound 12a (101 mg, 83%) as white solids. $^1$H NMR (CDCl$_3$, 200 MHz) δ 7.83 (d, J=9.0 Hz, 2H), 7.01 (d, J=9.0 Hz, 2H), 6.79 (s 1H), 6.57 (s, 1H), 4.72 (s, 2H), 3.99 (s 3H), 3.98 (s, 3H), 3.92 (s, 3H), 3.83 (s, 3H); $^{13}$C NMR (CDCl$_3$, 50 MHz) δ 177.1 (s), 168.7 (s), 160.7 (s), 160.0 (s), 157.6 (s), 154.4 (s), 152.5 (d), 140.3 (s), 127.6 (d, 2C), 124.9

(s), 114.9 (d, 2C), 112.8 (s), 107.3 (d), 96.2 (d), 65.0 (t), 62.1 (q), 61.4 (q), 56.2 (q), 52.3 (q).

Preparation of 6-(Carbethoxymethoxy)-5-hydroxy-4',7-dimethoxyflavone. Similar to the preparation of 4'-(carbmethoxymethoxy)-5,6,7-trimethoxyflavone, the title compound is prepared from a suspension of 5,6-dihydroxy-4',7-dimethoxyflavone (628 mg, 2 mmol), ethyl bromoacetate (367 mg, 2.2 mmol), and anhydrous potassium carbonate (0.5 g) in acetone (50 ml).

Preparation of 4'-(Carbethoxymethylamino)-5,6,7-trimethoxyflavone. Similar to the preparation of 12a, the title compound is prepared from the reaction of 4'-amino-5,6,7-trimethoxyflavone, 10a, (654 mg, 2 mmol), ethyl bromoacetate (367 mg, 2.2 mmol), and anhydrous potassium carbonate (0.5 g) in methanol (40 ml).

Preparation of 4'-[N-methyl-N-(3-methoxypropyl)amino)-5,6,7-trimethoxyflavone. Similar to the preparation of 12a, the title compound is prepared from the reaction of 10d and 3-methoxypropyl bromide in the presence of potassium carbonate.

Preparation of 4'-[N,N-di(2-hydroxyethyl)-amino)-5,7-dihydroxy-6-methoxyflavone and 4'-(2-hydroxyethylamino)-5,7-dihydroxy-6-methoxyflavone. Similar to the preparation of 10c and 10d, the title compounds are prepared from the reaction of 4'-amino-6-methoxylbaicalein (1.5 g, 5 mmol) (Phadke, P. S.; Rao, A. V. R.; Venkataraman, K. *Indian J. Chem.* 1967, 5, 131-3), 2-bromoethanol (749 mg, 6 mmol), and anhyd. potassium carbonate (1 g) in acetone (20).

Preparation of 4'-(2-methanesulfonatoethylamino)-5,7-dihydroxy-6-methoxyflavone. A solution of 4'-(2-hydroxyethylamino)-5,7-dihydroxy-6-methoxyflavone (1.72 g, 5 mmol) in methylene chloride (40 ml) at 0° C. under nitrogen is treated with mesyl chloride (801 mg, 10 mmol) dropwise followed by triethylamine (1.518 g, 15 mmol). The reaction mixture is kept at 0° C. for 1 h, warmed up to RT for 1 hr, and then poured into an ice-water mixture. The organic layer is separated and the aqueous layer is extracted with methylene chloride twice (40 ml×2). The organic layers are combined, washed with water followed by saturated brine and dried. A solid formed is collected and washed with a small amount of water and dried ($MgSO_4$), thus giving the expected mesylate upon evaporation of the dried solution.

Preparation of 4'-[2-(N,N-diethylamino)ethylamino]-5,7-dihydroxy-6-methoxyflavone. A solution of the mesylate, 4'-(2-methanesulfonatoethyiamino)-5,7-dihydroxy-6-methoxyflavone, (442 mg, 1 mmol), diethylamine (1 ml) and anhyd. THF (20 ml) is heated under reflux overnight. The reaction is cooled and evaporated to give the title compound.

Preparation of 6,7-methylenedioxy-5-hydroxy-4'-methoxy-flavone. A solution of Kanzakiflavone-1 or 6,7-methylenedioxy-5,4'-dihydroxyflavone (1.49 g, 5 mmol) [Manchanda, V. P.; Khanna, R. N. Curr. Sci. (1977), 46(13), 445-6.] and dimethylsulfate (1.02 g, 8 mmol) in acetone (20 ml) is refluxed in the presence of anyhd. potassium carbonate (0.5 g) overnight. The reaction mixture is filtered off and the filtrate is evaporated to give a dark brown residue. The residue is taken up in ethyl acetate and washed with water followed by saturated brine solution and dried ($MgSO_4$), thus giving the title compound, upon filtration and evaporation.

Preparation of 4'-[2-(N,N-diethylamino)ethoxy]-6,7-methylenedioxy-5-hydroxy-flavone. Similar to the preparation of 4'-[2-(N,N-diethylamino)ethylamino]-5,7-dihydroxy-6-methoxyflavone (discussed above), the title compound is prepared starting from 6,7-methylenedioxy-5,4'-dihydroxyflavone.

Preparation of 4'-(2,3-dihydroxy-propyloxy)-5,6,7-trimethoxyflavone. To a solution of 1 h (240 mg, 0.58 mmol) and 0.5 N NaOH (3 ml) is added 3-hydroxy-1,2-propyleneoxide (74 mg, 1 mmol) at RT with stirring. The reaction is followed by tlc. At the end of the reaction, the product is precipitated out, collected and purified by a silica gel column (1% methanol in ethyl acetate) to give the title compound.

Preparation of 2,3-diphenyl-5,6,7-trimethoxychromone. The title compound is prepared from heating a mixture of ω-phenyl-6-hydroxy-2,3,4-trimethoxy-acetophenone (0.996 g, 3.3 mmol), benzoic anhydride (6 g, 13.3 mmol) and sodium benzoate (6.5 g, 22.5 mmol) at 180-190° C. for 6 hr according to the published procedure (Wu, E S C et al. J. Med. Chem. 1988, 32, 183-192). Similar to the preparation ω-phenylresacetophenone (Wu, E S C et al. J. Med. Chem. 1987, 30, 788-792), ω-phenyl-6-hydroxy-2,3,4-trimethoxy-acetophenone is, in turn, obtained from adding anhydrous zinc chloride to a solution of 3,4,5-trimethoxyphenol and benzyl cyanide in ethyl acetate followed by bubbling HCl into the reaction mixture at room temperature and then heating at 95-100° C. with water.

Preparation of 2,3-diphenyl-5,6,7-trihydroxychromone. Similar to the preparation of 1d, the reaction of 2,3-diphenyl-5,6,7-trimethoxychromone with boron tribromide in methylene chloride at ° C. for 30 min and then at room temperature for 3 hr produces the title compound.

EXAMPLE 2

Pharmacological Testing

The pharmacological activity of the compounds of the present invention can be measured in the exemplary tests set out below.

Materials and Methods. Male Charles River Wistar-Kyoto rats (230-300 g) from Japan were used. The rats were anesthetized by intraperitoneal injection of urethane (1.2 g/kg). The trachea was cannulated to facilitate respiration and rectal temperature was maintained at 37° C. with a homeothermic blanket (Harvard Apparatus, South Natick, Mass.). The right carotid artery was cannulated and connected to a pressure transducer (P233ID, Statham, Oxnard, Calif.) for the measurement of phasic and mean arterial pressure as well as heart rate which were displayed on a Gould model TA5000 polygraph recorder (Gould, Valley View, Ohio). The left jugular vein was cannulated for the administration of drugs. Upon completion of the surgical procedure, cardiovascular parameters were allowed to stabilize for 20 min. After recording of the baseline hemodynamic parameters, the animals were given vehicle (DMSO) or baicalein (5, 10, or 20 mg/kg, i.v.). Baicalein was administered intravenously at 1 hour after lipopolysaccharide (LPS) administration. Prior to (i.e., at time 0) and at every hour after vehicle or LPS, 0.5 ml of blood was taken to measure the changes in plasma levels of TNF-α and nitrate (an indicator of NO formation (Yen, M. H. et al., *Shock* 14, 60-67, 2000). Any blood withdrawn was immediately replaced by the injection of an equal volume of saline.

Plasma TNF-α Determination. The plasma samples (100 μl) were diluted 1:2 and TNF-α was measured in duplicate with an enzyme linked immunoadsorbent assay (ELISA) kit (Genzyme, Cambridge, Mass.) (Yen, M. H. et al., *Biochem. Biophys. Res. Commun.* 228:459-466, 1996).

Superoxide Anion Detection by Chemiluminescence. Detection of superoxide was performed as previously described. Briefly, the aortas were cut into 5-mm rings and then incubated in Krebs-HEPES buffer containing 0.25 mmol/L lucigenin. Counts were obtained at 15-minute intervals at 37° C. with a luminescence measurement system (microLumate plus LB96V, EG&G Berthold).

Plasma Nitrate Determination. Determination of plasma nitrate was performed as previously described. Briefly, for the reduction of liquid nitrate to the gas NO, 10 µl was injected into a collection chamber containing 5% $VCl_3$. NO was carried by a constant stream of helium gas into a NO analyzer (Seivers 270B NOA, Seivers Instruments Inc.).

iNOS Detection by Western Blotting. Detection of inducible nitric oxide synthase (iNOS) by western blotting was performed as described previously. The primary antibodies probed in the experiment were mouse anti-iNOS (Transduction Laboratories).

Measurement of Serum glutamic oxaloacetic transaminase (SGOP) and Serum glutamic pyrate transaminase (SGTP). 10 µl of serum was taken out at 0 and 6 hr intervals and were added to slides of GOP and GTP and then placed in DRI-CHEM 3000 (Colorige Tric Analyzer; FUJIFILM; Tokyo, Japan.

Histological Studies. Lungs and livers were obtained from surviving mice in each group after the study (8 hr postdose) and these tissues were fixed in Carson-Millonig's solution for histopathological examination as described previously in Chen, A. et al. *Lab. Invest.* 67, 175-185 (1992). The fixed lung and liver tissues were dehydrated in graded ethanol and embedded in paraffin. Three-micron sections were stained with the hematoxylin and eosin reagent for light microscopy. In preliminary experiments, a pathological feature of the mice receiving LPS was an infiltration of neutrophils in the organs studied. This histological alteration was quantitatively analyzed as an index of the severity of tissue injury. This index was a neutrophil infiltration index which was determined by counting the numbers of neutrophils in 10 randomly selected high power fields. The index was expressed as the mean of these 10 numbers±standard error of the mean (SEM)/high power field.

The foregoing is illustrative of the present invention, and is not to be construed as limiting thereof. The invention is defined by the following claims, with equivalents of the claims to be included therein.

What is claimed is:

1. A compound according to formula I:

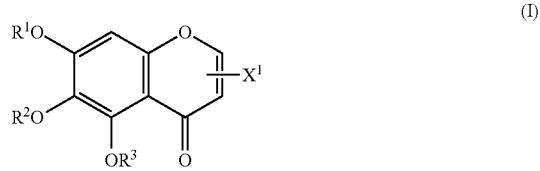

(I)

wherein:
R$^1$ and R$^3$ are each independently H, —SO$_3$H, or —PO$_3$H$_2$;
R$^2$ is selected from, —SO$_3$H or —PO$_3$H; and
X$^1$ is bound in the 2- or 3-position and is of the formula:

Ar—X$^3$ wherein—

Ar is phenyl and X$^3$ is selected from the group consisting of NR'R", NHR', hydroxyl. Alkoxy, carbooxyalkoxyalkoxy, hydroxyl(hydroxyalkyl)alkoxy and N,N-dialkylaminoalkoxy, wherein R' and R' are each independently selected from hydrogen, alkyl, N,N-(dialkylamino) alkyl, alkoxyalkyl, hydroxyalkyl, alkylsulfonyl and alkylsulfonato alkyl or pharmaceutically acceptable salts thereof.

2. The compound according to claim 1, wherein R$^1$, R$^2$ and R$^3$ are each independently SO$_3$H or PO$_3$H$_2$.

3. The compound wherein the compound is 4'-(N,N-dimethylamino)-5,6,7-trimethoxyflavone, 4'-(methylamino)-5,6,7-trimethoxyflavone, 4'-[N-methyl-N-(3-methoxypropyl)amino]-5,6,7-trimethoxyflavone, 4'-[N,N-di-(2-hydroxyethyl)-amino]-5,7-dihydroxy-6-methoxyflavone, 4'-(2-hydroxyethylamino)-5,7-dihydroxy-6-methoxyflavone, 4'-(2-methanesulfonatoethylamino)-5,7-dihydroxy-6-methoxyflavone, 4'42-(N,N-diethylamino)ethylamino]-5,7-dihydroxy-6-methoxyflavone, 2,3-diphenyl-5,6,7-trimethoxychromone, 2,3-diphenyl-5,6,7-trihydroxychromone, 4'-(methylsulfonamido)-5,6,7-trimethoxyflavone, 4'42-(N,N-diethylamino)ethoxy]-6,7-methylenedioxy-5-hydroxyflavone, 4'-(2,3-dihydroxy-propyloxy)-5,6,7-trimethoxyflavone, or 4'-(Carbmethoxymethoxy)-5,6,7-trimethoxyflavone.

4. A pharmaceutical formulation comprising a compound according to claim 1 and at least one pharmaceutically acceptable carrier, diluent, or excipient.

5. A method of improving conditions in or delaying progression of a condition associated with overproduction of TNF-α selected from the group consisting of rheumatoid arthritis, Crohn's disease, and ulcerative colitis, comprising administering to a subject in need thereof an effective amount of a compound according to claim 1.

6. A method of improving conditions in or delaying progression of a condition liver damage, lung damage or kidney damage or combinations thereof resulting from over production of TNF-α or superoxide anion radicals comprising administering to a subject in need thereof an effective amount of a compound according to claim 1.

7. A method of improving conditions in or delaying progression of a condition conditions selected from the group consisting of diseases associated with the overproduction of TNF-α and combinations thereof, comprising administering to a subject in need thereof, a pharmaceutical composition comprising a therapeutically effective amount of a compound selected from the group consisting of baicalein-6-sulfate, baicalein-6,7-disulfate, bacalein-6-phosphate, bacalein-6,7-diphosphate, baicalein-5,6,7-triphosphate, sodium and potassium salt derivatives thereof, and pharmaceutically acceptable salts thereof.

8. The method according to claim 7, wherein the pharmaceutical composition is administered in combination with at least one other therapeutic agent useful for the treatment of conditions associated with overproduction of TNF-α.

9. A method of improving conditions in or delaying progression of a condition selected from the group consisting of diseases associated with the overproduction of TNF-α, and combinations thereof, comprising administering to a subject in need thereof, a pharmaceutical composition comprising a therapeutically effective amount of compound as in claim 3.

10. A pharmaceutical formulation comprising a compound according to claim 3 and at least one pharmaceutically acceptable carrier, diluent, or excipient.

* * * * *